US008541613B2

United States Patent
Nokura et al.

(10) Patent No.: US 8,541,613 B2
(45) Date of Patent: Sep. 24, 2013

(54) PROCESS FOR PRODUCING AMIDE COMPOUND

(71) Applicant: Sumitomo Chemical Company, Limited, Tokyo (JP)

(72) Inventors: Yoshihiko Nokura, Toyonaka (JP); Hiroshi Ikegami, Ikeda (JP); Markus Jachmann, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/745,449

(22) Filed: Jan. 18, 2013

(65) Prior Publication Data
US 2013/0131371 A1   May 23, 2013

Related U.S. Application Data

(62) Division of application No. 12/595,471, filed as application No. PCT/JP2008/057376 on Apr. 9, 2008, now Pat. No. 8,394,838.

(30) Foreign Application Priority Data

Apr. 11, 2007 (JP) ................................ 2007-103614

(51) Int. Cl.
   *C07C 335/16* (2006.01)
   *C07C 335/04* (2006.01)
   *C07C 269/00* (2006.01)

(52) U.S. Cl.
   USPC ............. 560/24; 560/123; 560/138; 560/161; 560/182

(58) Field of Classification Search
   CPC .. C07C 335/16; C07C 335/04; C07C 335/34; C07C 235/34; C07C 210/08; C07C 210/14; C07C 237/22
   USPC ............................ 560/24, 123, 138, 161, 182
   See application file for complete search history.

(56) References Cited

U.S. PATENT DOCUMENTS
7,867,949 B2   1/2011   Ikegami et al.
2004/0209923 A1   10/2004   Berger et al.

FOREIGN PATENT DOCUMENTS
| CN | 1713819 A | 12/2005 |
|---|---|---|
| EP | 0639559 B1 | 10/1997 |
| WO | WO 01/70671 A2 | 9/2001 |
| WO | WO 03/015518 A1 | 2/2003 |
| WO | WO 03/024222 A1 | 3/2003 |
| WO | WO 2007 043677 A1 * | 4/2007 |
| WO | WO 2007/043677 A1 | 4/2007 |

OTHER PUBLICATIONS

Official Action No. 3291 for corresponding Colombian Patent Application No. 9-111587, dated Feb. 18, 2013.
Chilean Office Action, dated Sep. 15, 2010, for Chilean Application No. 979-08.
Egyptian Office Action issued on Apr. 6, 2011 in Egyptian Patent Application No. PCT 1491/2009 with English language translation.
Ikegami et al. "Hydrazide compound and their preparation, formulation and pesticidal use," XP002496351 retrieved from STN Database, Accession No. 2007: 435753.
International Preliminary Report on Patentability (Form PCT/IB/373) and Written Opinion of the International Searching Authority (Form PCT/ISA/237) issued on Oct. 13, 2009 in PCT/JP2008/057376.
Lahm et al., "Insecticidal anthranilic diamides: A new class of potent ryanodine receptor activators," Bioorganic & Medicinal Chemistry Letters, vol. 15, No. 22, Nov. 15, 2005, pp. 4898-4906.
Mexican Office Action for Application No. MX/a/2009/010846 dated Nov. 3, 2011 (with English translation).
Office Action for corresponding European Patent Application No. 08740462.0, dated Aug. 13, 2012.
Russian Office Action for Application No. 2009141612/04 dated Dec. 8, 2011 (with English translation).
Second Office Action for corresponding Chinese Patent Application No. 200880019219.9. dated Feb. 16, 2013.
Examination Report for corresponding Taiwanese Patent Application No. 097112802, dated Feb. 6, 2013.

* cited by examiner

*Primary Examiner* — Johann R. Richter
*Assistant Examiner* — Blaine G Doletski
(74) *Attorney, Agent, or Firm* — Birch, Stewart, Kolasch & Birch, LLP

(57) ABSTRACT

There is provided a process for producing an amide compound having an excellent harmful arthropod-controlling activity and represented by the formula (3):

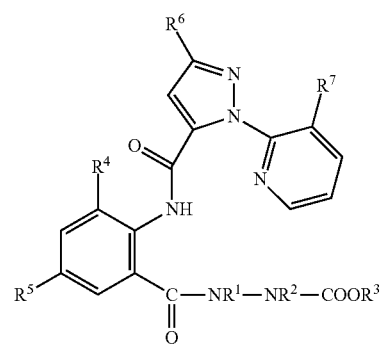

(3)

wherein $R^1$, $R^2$ and $R^3$ independently represent a C1-C6 alkyl group optionally substituted with at least one halogen atom etc., $R^4$, $R^5$, $R^6$ and $R^7$ independently represent a halogen atom etc.

5 Claims, No Drawings

PROCESS FOR PRODUCING AMIDE COMPOUND

TECHNICAL FIELD

The present invention relates to a novel process for producing an amide compound, intermediated compounds thereof, and the like.

BACKGROUND ART

To date, many compounds for controlling harmful arthropods have been developed and come into practical use. WO 01/70671 and WO 03/015518 disclose certain amide compounds having an arthropod-controlling activity.

DISCLOSURE OF THE INVENTION

The present inventors studied intensively a process for producing an amide compound having an excellent controlling activity on harmful arthropods represented by the following formula (3):

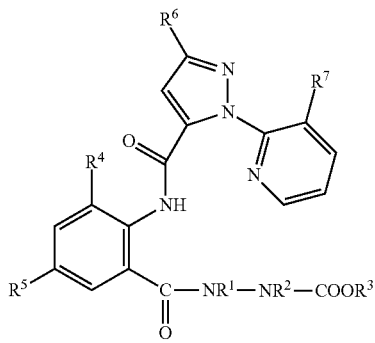

(3)

wherein $R^4$ represents a C1-C6 alkyl group optionally substituted with at least one halogen atom, $R^2$ represents a hydrogen atom, or a C1-C6 alkyl group optionally substituted with at least one halogen atom, $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom, $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ represents a halogen atom, or a C1-C6 alkyl group optionally substituted with at least one halogen atom and, as a result, completed the present invention. The present invention provides:

[1] a process for producing an amide compound represented by the formla (3):

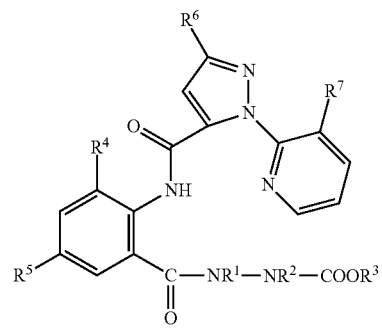

(3)

wherein $R^4$ represents a C1-C6 alkyl group optionally substituted with at least one halogen atom, $R^2$ represents a hydrogen atom, or a C1-C6 alkyl group optionally substituted with at least one halogen atom, $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom, $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ represents a halogen atom, or a C1-C6 alkyl group optionally substituted with at least one halogen atom (hereinafter referred to as the compound (3)), which comprises reacting an aniline compound represented by the formula (1):

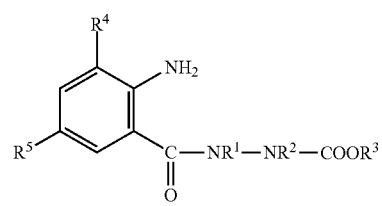

(1)

wherein $R^1$, $R^2$, $R^3$, $R^4$ and $R^5$ are as defined above (hereinafter referred to as the compound (1)), with an aldehyde compound represented by the formula (2):

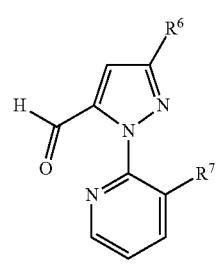

(2)

wherein $R^6$ and $R^7$ are as defined above (hereinafter referred to as the compound (2)), in a solvent in the presence of a quinone compound;

[2] the process according to the above [1], wherein the quinone compound is a compound selected from the group consisting of 2,3-dichloro-5,6-dicyano-1,4-benzoquinone, tetrachloro-1,2-benzoquinone, and tetrachloro-1,4-benzoquinone;

[3] an aniline compound represented by the formula (1):

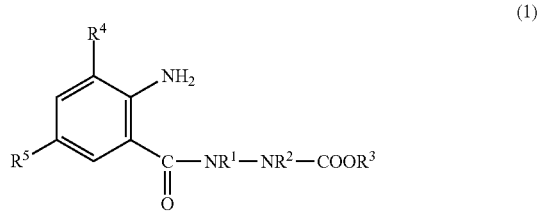

(1)

wherein $R^1$ represents a C1-C6 alkyl group optionally substituted with at least one halogen atom, $R^2$ represents a hydrogen atom, or a C1-C6 alkyl group optionally substituted with at least one halogen atom, $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom;

[4] the aniline compound according to the above [3], wherein $R^4$ represents a methyl group or an ethyl group, and $R^2$ represents a hydrogen atom, a methyl group or an ethyl group;

[5] the aniline compound according to the above [4], wherein $R^4$ and $R^2$ each represent a methyl group;

[6] the aniline compound according to the above [4], wherein $R^4$ represents a methyl group and $R^2$ represents a hydrogen atom;

[7] the aniline compound according to the above [4], wherein $R^4$ represents an ethyl group and $R^2$ represents a hydrogen atom;

[8] an aldehyde compound represented by the formula (2):

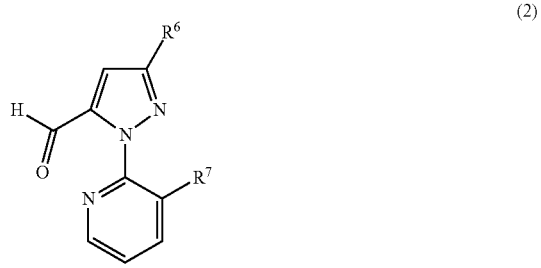

(2)

wherein $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ represents a halogen atom, or a C1-C6 alkyl group optionally substituted with at least one halogen atom;

[9] the aldehyde compound according to the above [8], wherein $R^6$ represents a halogen atom or a C1-C6 alkyl group optionally substituted with at least one halogen atom;

[10] the aldehyde compound according to the above [9], wherein $R^6$ represents a halogen atom or a trifluoromethyl group;

[11] the aldehyde compound according to the above [10], wherein $R^6$ represents a chlorine atom or a trifluoromethyl group, and $R^7$ represents a chlorine atom;

[12] an amide compound represented by the formula (3a):

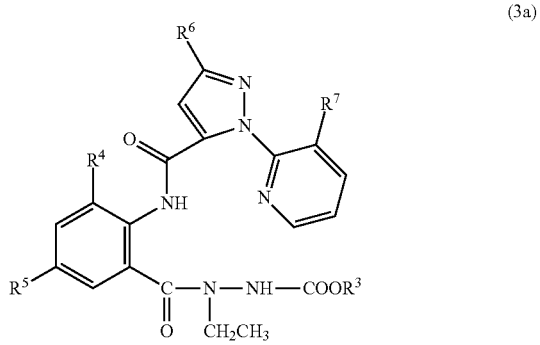

(3a)

wherein $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom, $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ represents a halogen atom, or a C1-C6 alkyl group optionally substituted with at least one halogen atom;

[13] the amide compound according to the above [12], wherein $R^3$ represents a methyl group, $R^4$ represents a chlorine atom, a bromine atom or a methyl group, $R^5$ represents a chlorine atom, a bromine atom or a cyano group, $R^6$ represents a chlorine atom, a bromine atom or a trifluoromethyl group, and $R^7$ represents a chlorine atom;

[14] a pesticidal composition comprising the amide compound according to the above [12] or [13] as an active ingredient;

[15] use of the amide compound according to the above [12] or [13] as an active ingredient for a pesticidal composition;

[16] a method of controlling a harmful arthropod which comprises applying the amide compound according to the above [12] or [13] directly to the harmful arthropod, or to a place where the harmful arthropod inhabits;

[17] use of the amide compound according to the above [12] or [13] for manufacturing a pesticidal composition;

[18] a compound represented by the formula (17):

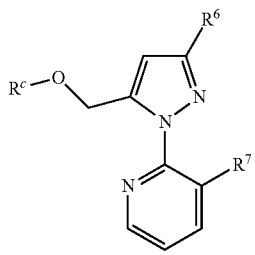

(17)

wherein $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ represents a halogen atom, or a C1-C6 alkyl group optionally substituted with at least one halogen atom, and $R^c$ represents a C1-C4 alkyl group;

[19] the compound according to the above [18], wherein $R^6$ represents a halogen atom or a C1-C6 alkyl group optionally substituted with at least one halogen atom; and the like.

According to the process of the present invention, the compound (3) having an excellent controlling activity on harmful arthropods can be produced.

BEST MODE FOR CARRYING OUT THE INVENTION

In the process of the present invention, usually 0.5 to 2 mol of the compound (2) is used per 1 mol of the compound (1). The used amounts of the compound (1) and the compound (2) may be varied depending on the reaction situation.

The reaction of the compound (1) with the compound (2) is performed in the presence of a quinone compound. The quinone compound as used herein refers to a compound obtained by replacing two of CH atomic groups in an aromatic compound with CO atomic groups, and then moving double bonds so as to form quinoid structure. Quinone compounds are roughly classified into p-quinone compounds and o-quinone compounds on the basis of quinoid structure, and p-quinone compounds and o-quinone compounds have the following basic structure (a) and (b) respectively.

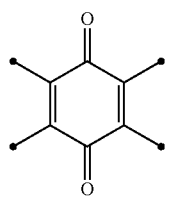

(a)

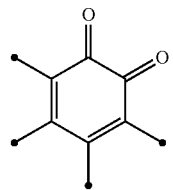

(b)

Examples of the quinone compound include p-quinone compounds such as 2,3-dichloro-5,6-dicyano-1,4-benzoquinone (DDQ), tetrachloro-1,4-benzoquinone (p-chloranil) and the like, and o-quinone compounds such as tetrachloro-1,2-benzoquinone (o-chloranil) and the like. In the process of the present invention, p-chloranil or o-chloranil is preferably used.

The amount of the quinone compound used in the reaction is preferably 1 to 2 mol per 1 mol of the compound (2), and the used amount may be varied depending on the reaction situation. Alternatively, the reaction can be performed using less than 1 mol, that is, a catalytic amount of the quinone compound and not less than 1 mol of a co-oxidizing agent per 1 mol of the compound (2). In the case of using a catalytic amount of the quinone compound, examples of the co-oxidizing agent which can be used include oxygen, hydrogen peroxide, alkyl hydroperoxide, percarboxylic acid, sodium hypochlorite and the like.

The reaction is performed in a solvent. Examples of the solvent which can be used include ether solvents such as 1,4-dioxiane, diethyl ether, tetrahydrofuran, methyl tert-butyl ether and the like; halogenated hydrocarbon solvents such as dichloromethane, chloroform, carbon tetrachloride, 1,2-dichloroethane, chlorobenzene and the like; hydrocarbon solvents such as hexane, heptane, toluene, benzene, xylene and the like; nitrile solvents such as acetonitrile and the like; amide solvents such as N,N-dimethylformamide and the like; nitrogen-containing cyclic compound solvents such as N-methylpyrrolidone, 1,3-dimethyl-2-imidazolidinone and the like; aprotic solvents, for example, sulfoxide solvents such as dimethyl sulfoxide; carboxylic acid solvents such as acetic acid and the like; ketone solvents such as acetone, isobutyl methyl ketone and the like; ester solvents such as ethyl acetate and the like; alcohol solvents such as 2-propanol, tert-butyl alcohol and the like; and water. Two or more of the above-mentioned solvents may be used as a mixture, and the reaction may be performed in a single-phase system or a two-phase system.

The temperature of the reaction is usually in a range of 0 to 150° C., and the reaction time is usually in a range of instant to 72 hours.

In the reaction, an acid may be present as necessary. Examples of the acid which can be used include mineral acids such as hydrochloric acid, sulfuric acid, nitric acid, phosphoric acid, perchloric acid and the like; carboxylic acids such as acetic acid, benzoic acid and the like; sulfonic acids such as methanesulfonic acid, benzenesulfonic acid, p-toluenesulfonic acid and the like; boron compounds such as boron trifluoride and the like; aluminum compounds such as aluminum(III) chloride, aluminum(III) isopropoxide and the like; titanium compounds such as titanium(IV) tetrachloride, titanium(IV) isopropoxide and the like; zinc compounds such as zinc(II) chloride; iron compounds such as iron(III) chloride and the like.

In the case of using an acid in the reaction, the amount of the acid used is usually 0.001 to 1 mol per 1 mol of the compound (2), and the used amount may be varied depending on the reaction situation.

After completion of the reaction, the reaction mixture is poured into water and then extracted with an organic solvent, or the reaction mixture is poured into water and formed precipitates are collected by filtration, thereby the compound (3) can be isolated. The isolated compound (3) can be further purified by recrystallization, chromatography or the like.

Then, a process for producing the compound (1) and the compound (2) used in the process of the present invention will be explained.

The compound (1) can be produced according to Scheme (1).

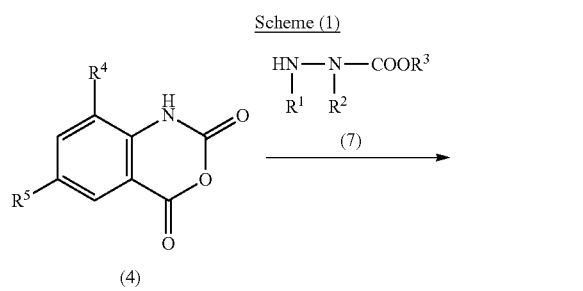

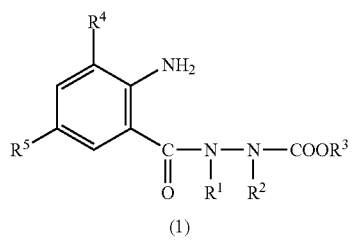

wherein, $R^1$, $R^2$, $R^3$, $R^4$ and $R^5$ are as defined above.

[Compound (4)→Compound (1)]

The amount of the compound (7) used is usually 1 mol per 1 mol of compound (4).

The reaction is usually performed in the presence of a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

Among the compounds (1), a compound represented by the formula (1-i) can be produced according to Scheme (2).

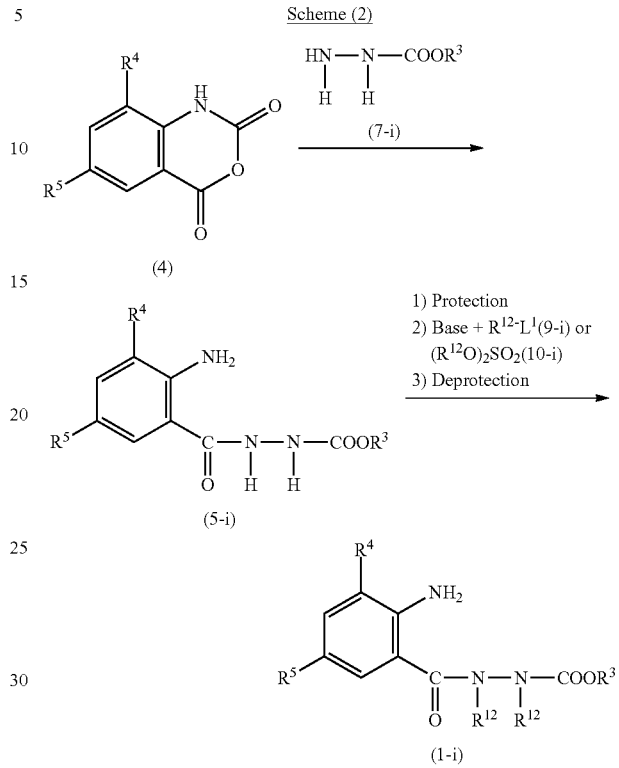

wherein, $R^{12}$ represents a C1-C6 alkyl group optionally substituted with at least one halogen atom, $L^1$ represents a leaving group (e.g. a halogen atom, a methanesulfonyloxy group or a p-toluenesulfonyloxy group), and $R^3$, $R^4$ and $R^5$ are as defined above.

[Compound (4)→Compound (5-i)]

The amount of the compound (7-i) used is usually 1 mol per 1 mol of the compound (4).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

[Compound (5-i)→Compound (1-i)]
1) Protection

The amino group (—$NH_2$) on the benzene ring of the compound (5-i) can be protected with a suitable protecting group (e.g. N-benzylidene group, N-(1-methyl)ethylidene group) described in Greene's Protective Groups in Organic Synthesis (WILEY) etc., if necessary.

2) Base+$R^{12}$-$L^1$ (9-i) or $(R^{12}O)_2SO_2$ (10-i)

The amount of the compound (9-i) or the compound (10-i) used is usually 2 mol per 1 mol of the compound (5-i) or a derivative thereof in which the amino group is protected. Examples of a base used in the reaction include metal carbonates such as potassium carbonate, sodium carbonate and the like, metal hydroxides such as lithium hydroxide, sodium hydroxide, potassium hydroxide and the like, and metal hydrides such as sodium hydride and the like.

3) Deprotection

The compound (1-i) in which the amino group is protected can be deprotected under known conditions.

Among the compounds (1), a compound represented by the formula (1-ii) can be produced according to Scheme (3).

3) Deprotection

The compound (1-ii) in which the amino group is protected can be deprotected under known conditions.

Among the compounds (1), a compound represented by the formula (1-iii) can be produced according to Scheme (4).

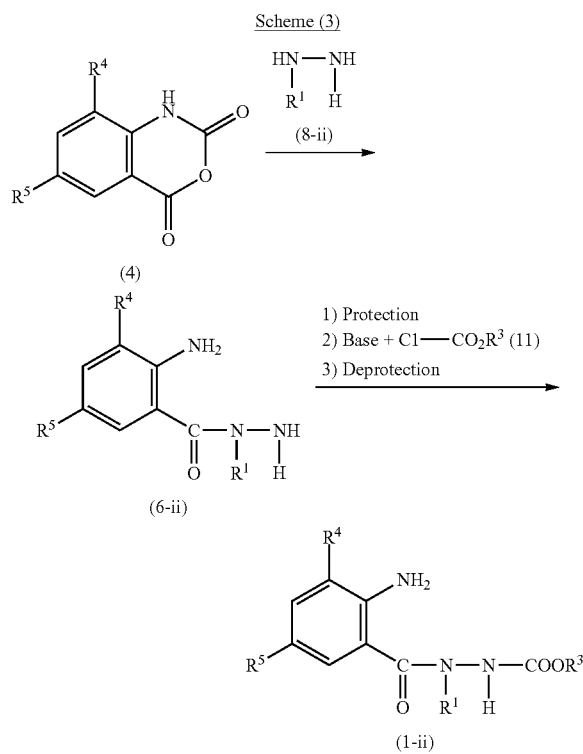

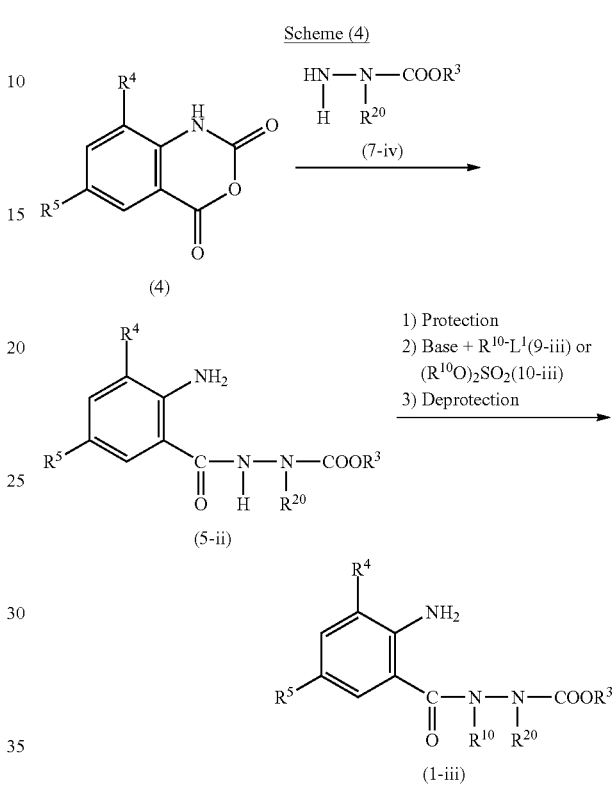

wherein $R^1$, $R^3$, $R^4$ and $R^5$ are as defined above.

[Compound (4)→Compound (6-ii)]

The amount of the compound (8-ii) used is usually 1 mol per 1 mol of the compound (4).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

[Compound (6-ii)→Compound (1-ii)]

1) Protection

The amino group (—NH$_2$) on the benzene ring of the compound (6-ii) can be protected with a suitable protecting group (e.g. N-benzylidene group, N-(1-methyl)ethylidene group) described in Greene's Protective Groups in Organic Synthesis (WILEY) etc., if necessary.

2) Base+Cl—CO$_2$R$^3$ (11)

The amount of the compound (11) used is usually 1 mol per 1 mol of the compound (6-ii) or a derivative thereof in which the amino group is protected. Examples of a base used in the reaction include metal carbonates such as sodium carbonate, potassium carbonate, cesium carbonate and the like, metal hydroxides such as lithium hydroxide, sodium hydroxide, potassium hydroxide and the like, and metal hydrides such as sodium hydride and the like.

wherein, $R^{10}$ and $R^{20}$ represent a C1-C6 alkyl group optionally substituted with at least one halogen atom, and $R^3$, $R^4$, $R^5$ and $L^1$ are as defined above.

[Compound (4)→Compound (5-ii)]

The amount of the compound (7-iv) used is usually 1 mol per 1 mol of the compound (4).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

[Compound (5-ii)→Compound (1-iii)]

1) Protection

The amino group (—NH$_2$) on the benzene ring of the compound (5-ii) can be protected with a suitable protecting group (e.g. N-benzylidene group, N-(1-methyl)ethylidene group) described in Greene's Protective Groups in Organic Synthesis (WILEY) etc., if necessary.

2) Base+$R^{10}$-$L^1$ (9-iii) or ($R^{10}$O)$_2$SO$_2$ (10-iii)

The amount of the compound (9-iii) or the compound (10-iii) used is usually 1 mol per 1 mol of the compound (5-ii) or a derivative thereof in which the amino group is protected. Examples of a base used in the reaction include metal carbonates such as sodium carbonate, potassium carbonate, cesium carbonate and the like, metal hydroxides such as lithium hydroxide, sodium hydroxide, potassium hydroxide and the like, and metal hydrides such as sodium hydride and the like.

3) Deprotection

The compound (1-iii) in which the amino group is protected can be deprotected under known conditions.

The compound (4) is a known compound, or can be produced according to the following Scheme (5).

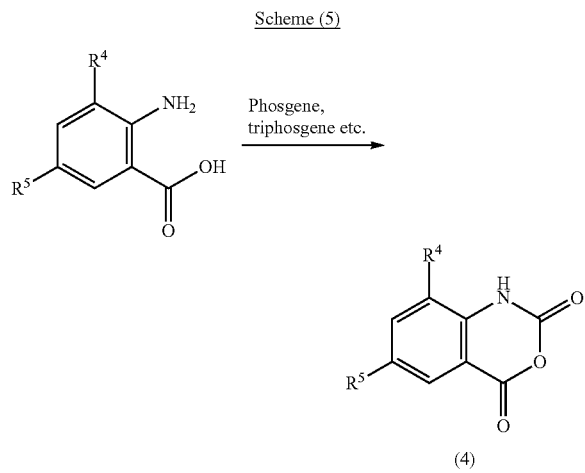

wherein $R^4$ and $R^5$ are as defined above.

The compounds (7-i), (7-ii), (7-iii) and (7-iv) are known compounds, or can be produced according to the following Scheme (6).

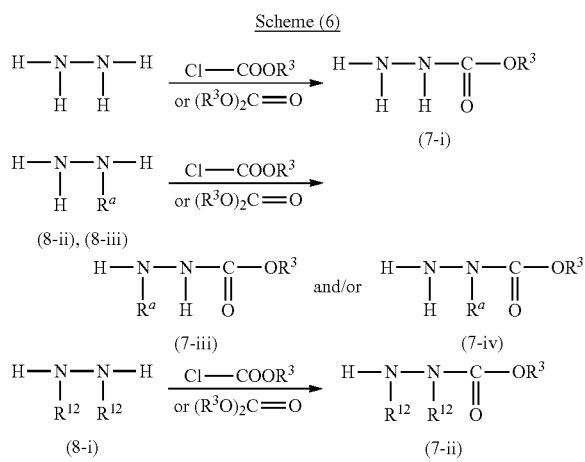

wherein, $R^8$ represents a C1-C6 alkyl group optionally substituted with at least one halogen atom, and $R^3$ and $R^{12}$ are as defined above.

The compounds (8-i), (8-ii) and (8-iii) are known compounds, or can be produced from known compounds according to known methods (see, for example, Organic Functional Group Preparations, 2nd edition, Vol. 1, chapter 14, p. 434-465, Stanley R. Sandler, Wolf Karo.).

Among the compounds (7), a compound represented by the formula (7-v) can be produced according to Scheme (7).

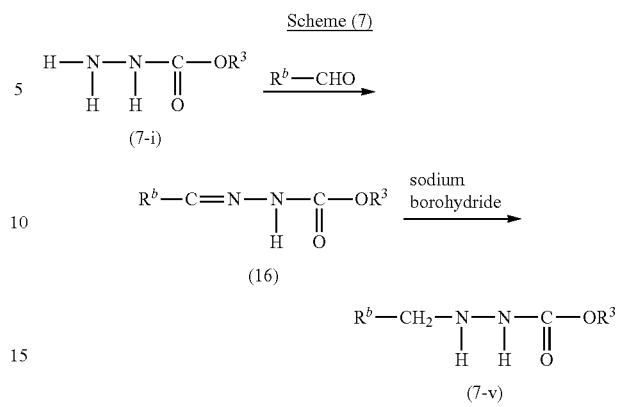

wherein Rb represents a C1-C5 alkyl group optionally substituted with at least one halogen atom, and $R^3$ is as defined above.

[Compound (7-i)→Compound (16)]

The amount of $R^b$—CHO used is usually 1 to 2 mol per 1 mol of the compound (7-i).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

[Compound (16)→Compound (7-v)]

The amount of sodium borohydride used is usually 0.25 to 2 mol per 1 mol of the compound (16).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, alcohols such as methanol, ethanol, isopropyl alcohol and the like, and a mixture thereof.

The compound (2) can be produced according to a method, for example, shown in the following Scheme (8).

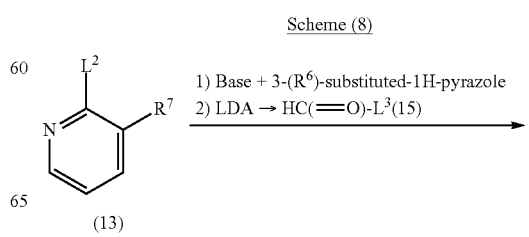

13
-continued

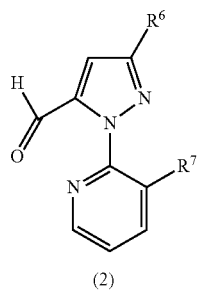

(2)

wherein, $L^2$ represents a leaving group (e.g. halogen atom, methylsulfonyl group etc.), $L^3$ represents a leaving group (e.g. methoxy group, ethoxy group, N,N-dimethylamino group, 1-imidazolyl group etc.), and $R^6$ and $R^7$ are as defined above.

[Compound (13)→Compound (2)]
1) Base+3-($R^6$)-substituted-1H-pyrazole

The amount of the 3-($R^6$)-substituted-1H-pyrazole used is usually 1 mol per 1 mol of the compound (13). Examples of a base used in the reaction include metal carbonates such as sodium carbonate, potassium carbonate, cesium carbonate and the like, metal hydroxides such as lithium hydroxide, sodium hydroxide, potassium hydroxide and the like, and metal hydrides such as sodium hydride and the like.

The reaction is usually performed in a solvent. Examples of the solvent include ethers such as 1,4-dioxane, diethyl ether, tetrahydrofuran, methyl tert-butyl ether and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, and a mixture thereof.

2) LDA, then HC(=O)-$L^3$ (15)

The amount of LDA (lithium diisopropylamide) used is usually 1 mol and the amount of the compound (15) used is usually 1 mol, per 1 mol of 2-[3-($R^6$)-substituted-1H-pyrazol-1-yl]-3-($R^7$)-substituted pyridine.

The reaction is usually performed in a solvent. Examples of the solvent include ethers such as 1,4-dioxane, diethyl ether, tetrahydrofuran, methyl tert-butyl ether and the like, hydrocarbons such as toluene, benzene, xylene and the like, and a mixture thereof.

The compound (13) is a known compound, or can be produced from a known compound according to a known method.

14

The compound (2) can also be produced according to a method, for example, shown in the following Scheme (9).

Scheme (9)

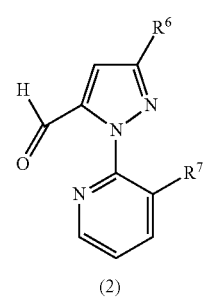

wherein $R^c$ represents a C1-C4 alkyl group, and $R^6$ and $R^7$ are as defined above.

Examples of an oxidizing agent used in the reaction include persulfates such as sodium persulfate, potassium persulfate, ammonium persulfate and the like. The amount of the oxidizing agent used is usually 1 to 2 mol per 1 mol of the compound (17).

The reaction is usually performed in a solvent. Examples of the solvent include nitriles such as acetonitrile and the like, water and a mixture thereof.

Among the compounds (17), a compound represented by the formula (17-i) can be produced, for example, according to Scheme (10).

Scheme (10)

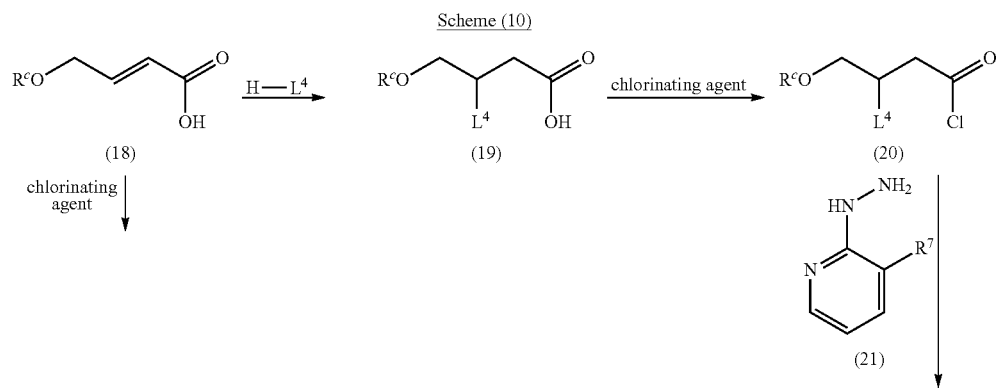

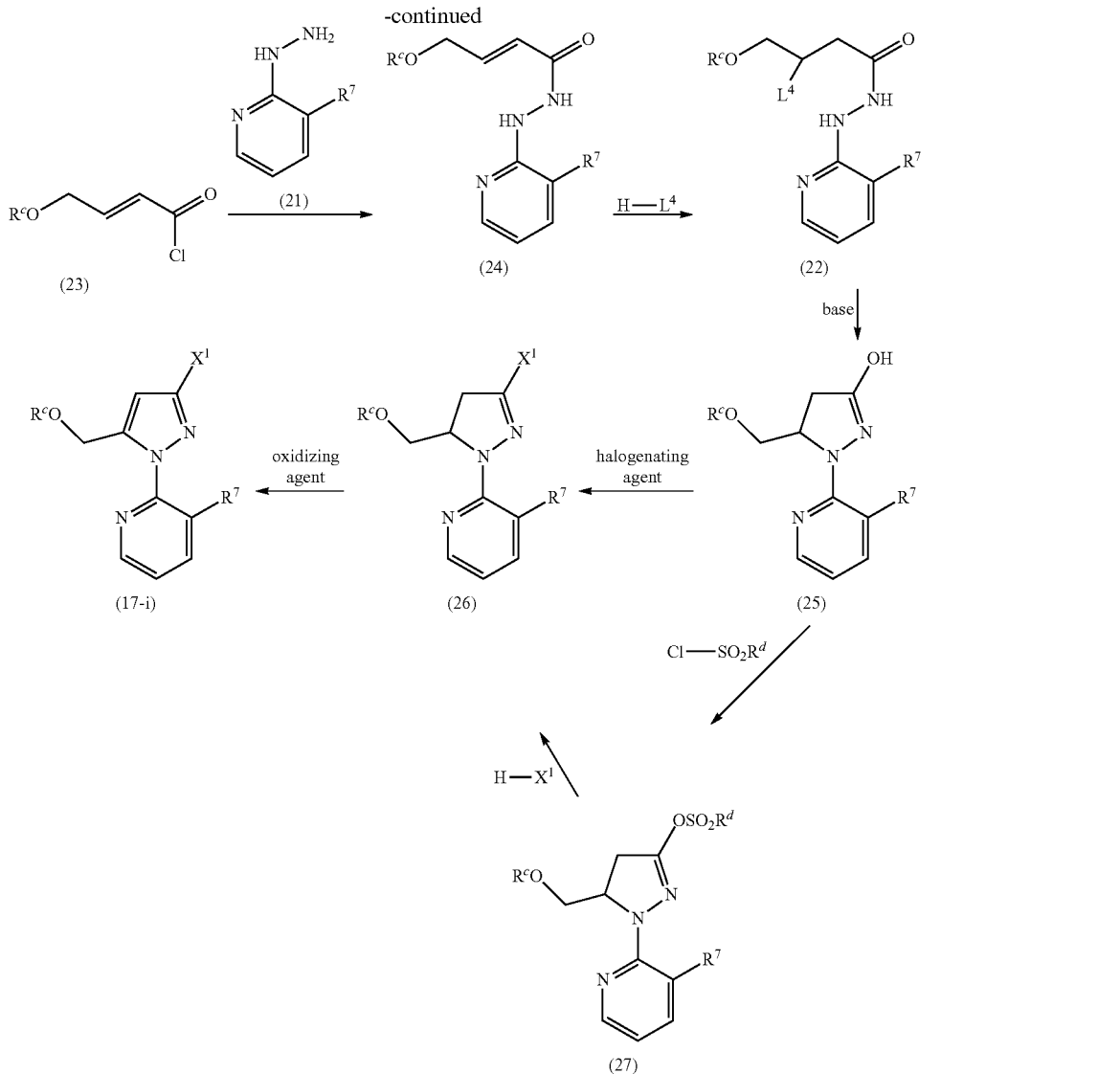

wherein $R^d$ represents a methyl group, a phenyl group or a p-tolyl group, $L^4$ represents a chlorine atom or a bromine atom, $X^4$ represents a halogen atom, and $R^c$ and $R^7$ are as defined above.

[Compound (18)→Compound (19)]

Examples of H-$L^4$ include hydrogen chloride and hydrogen bromide.

The reaction is usually performed in a solvent. Examples of the solvent include ethers such as 1,4-dioxane, diethyl ether, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, and a mixture thereof.

[Compound (19)→Compound (20)]

Examples of a chlorinating agent used in the reaction include oxalyl dichloride, thionyl chloride and the like. The amount of the chlorinating agent used is usually 1 to 10 mol per 1 mol of the compound (19).

The reaction is performed under a solventless condition or in a solvent. Examples of the solvent include ethers such as 1,4-dioxane, diethyl ether, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, and a mixture thereof.

[Compound (20)→Compound (22)]

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, and a mixture thereof.

The amount of the compound (21) used in the reaction is usually 1 mol per 1 mol of the compound (20).

The reaction is performed in the presence of a base, as necessary. Example of the base include nitrogen-containing heterocyclic compounds such as pyridine, picoline, 2,6-lutidine 1,8-diazabicyclo[5.4.0]7-undecene (DBU), 1,5-diazabicyclo[4.3.0]5-nonene (DBN) and the like, tertiary amines such as triethylamine, N,N-diisopropylethylamine and the like, and the like. The amount of the base used is usually 1 mol or more per 1 mol of the compound (20).

[Compound (18)→Compound (23)]

Examples of a chlorinating agent used in the reaction include oxalyl dichloride, thionyl chloride and the like. The amount of the chlorinating agent used is usually 1 to 10 mol per 1 mol of the compound (18).

The reaction is performed under a solventless condition or in a solvent. Examples of the solvent include ethers such as 1,4-dioxane, diethyl ether, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, and a mixture thereof.

[Compound (23)→Compound (24)]

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, and a mixture thereof.

The amount of the compound (21) used in the reaction is usually 1 mol per 1 mol of the compound (23).

The reaction is performed in the presence of a base, as necessary. Example of the base include nitrogen-containing heterocyclic compounds such as pyridine, picoline, 2,6-lutidine 1,8-diazabicyclo[5.4.0]7-undecene (DBU), 1,5-diazabicyclo[4.3.0]5-nonene (DBN) and the like, tertiary amines such as triethylamine, N,N-diisopropylethylamine and the like, and the like. The amount of the base used is usually 1 mol or more per 1 mol of the compound (23).

[Compound (24)→Compound (22)]

Examples of H—$L^4$ include hydrogen chloride and hydrogen bromide.

The reaction is usually performed in a solvent. Examples of the solvent include ethers such as 1,4-dioxane, diethyl ether, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, and a mixture thereof.

[Compound (22)→Compound (25)]

The reaction is performed in the presence of a base. Examples of the base used in the reaction include metal carbonates such as sodium carbonate, potassium carbonate, sodium hydrogen carbonate, potassium hydrogen carbonate, calcium carbonate, cesium carbonate and the like. The amount of the base used is usually 1 mol or more per 1 mol of the compound (22).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, and a mixture thereof.

[Compound (25)→Compound (26)]

Examples of a halogenating agent used in the reaction include oxalyl dichloride, thionyl chloride, phosphorus oxychloride, phosphorus pentachloride, thionyl bromide, phosphorus oxybromide, phosphorus pentabromide and the like. The amount of the halogenating agent used is usually 1 to 10 mol per 1 mol of the compound (25).

The reaction is performed under a solventless condition or in a solvent. Examples of the solvent include ethers such as 1,4-dioxane, diethyl ether, methyl tert-butyl ether and the like, halogenated hydrocarbons such as dichloromethane, chloroform, carbon tetrachloride, 1,2-dichloroethane, chlorobenzene and the like, hydrocarbons such as toluene, benzene, xylene and the like, nitriles such as acetonitrile and the like, and a mixture thereof.

[Compound (25)→Compound (27)]

Examples of Cl—$SO_2R^d$ include methanesulfonyl chloride, benzenesulfonyl chloride, p-toluenesulfonyl chloride and the like. The amount of Cl—$SO_2R^d$ used is usually 1 mol per 1 mol of the compound (25).

The reaction is usually performed in a solvent. Examples of the solvent include ethers such as 1,4-dioxane, diethyl ether, tetrahydrofuran, methyl tert-butyl ether and the like, halogenated hydrocarbons such as dichloromethane, dibromomethane, chloroform, bromoform, carbon tetrachloride, 1,2-dichloroethane, chlorobenzene and the like, hydrocarbons such as toluene, benzene, xylene and the like, nitriles such as acetonitrile and the like, aprotic polar solvents such as N,N-dimethylformamide, N-methylpyrrolidone, 1,3-dimethyl-2-imidazolidinone, dimethyl sulfoxide and the like, and a mixture thereof.

The reaction is performed in the presence of a base, as necessary. Example of the base include nitrogen-containing heterocyclic compounds such as pyridine, picoline, 2,6-lutidine 1,8-diazabicyclo[5.4.0]7-undecene (DBU), 1,5-diazabicyclo[4.3.0]5-nonene (DBN) and the like, tertiary amines such as triethylamine, N,N-diisopropylethylamine and the like, and the like. The amount of the base used is usually 1 mol or more per 1 mol of the compound (25).

[Compound (27)→Compound (26)]

Examples of H—$X^2$ include hydrogen chloride and hydrogen bromide.

The reaction is usually performed in a solvent. Examples of the solvent include ethers such as 1,4-dioxane, diethyl ether, methyl tert-butyl ether and the like, halogenated hydrocarbons such as dichloromethane, dibromomethane, chloroform, bromoform, carbon tetrachloride, 1,2-dichloroethane, chlorobenzene and the like, hydrocarbons such as toluene, benzene, xylene and the like, carboxylic acids such as acetic acid and the like, and a mixture thereof.

[Compound (26)→Compound (17-i)]

Examples of an oxidizing agent used in the reaction include persulfates such as sodium persulfate, potassium persulfate, ammonium persulfate and the like, quinone compounds such as 2,3-dichloro-5,6-dicyano-1,4-benzoquinone (DDQ), tetrachloro-1,4-benzoquinone (p-chloranil), tetrabromo-1,4-benzoquinone (p-bromanil), tetrachloro-1,2-benzoquinone (o-chloranil), tetrabromo-1,2-benzoquinone (o-bromanil) and the like, halogens such as chlorine, bromine and the like, air, and the like.

In the case of using a persulfate as the oxidizing agent, the amount of the oxidizing agent is usually 1 to 2 mol per 1 mol of the compound (26), and the reaction is usually performed in a solvent and examples thereof include nitriles such as acetonitrile and the like; water; and a mixture thereof.

In the case of using a quinone compound as the oxidizing agent, the amount of the oxidizing agent is usually 1 to 2 mol per 1 mol of the compound (26). The reaction is usually performed in a solvent and examples of thereof include ethers such as 1,4-dioxane, diethyl ether, tetrahydrofuran, methyl tert-butyl ether and the like; halogenated hydrocarbons such as dichloromethane, chloroform, bromoform, carbon tetrachloride, 1,2-dichloroethane, chlorobenzene and the like; hydrocarbons such as hexane, heptane, toluene, benzene, xylene and the like; nitriles such as acetonitrile and the like; amides such as N,N-dimethylformamide and the like; nitrogen-containing heterocyclic compounds such as N-methylpyrrolidone, 1,3-dimethyl-2-imidazolidinone, and the like; aprotic polar solvents, for example, sulfoxide solvents such as dimethyl sulfoxide and the like; carboxylic acids such as acetic acid and the like; ketones such as acetone, isobutyl methyl ketone and the like; esters such as ethyl acetate and the like; alcohols such as 2-propanol, tert-butyl alcohol and the like, and water. Two or more of the above-mentioned solvents may be used as a mixture, and the reaction may be performed in a single-phase system or a two-phase system.

In the case of using a halogen atom as the oxidizing agent, the reaction is performed in the presence of a solvent and a base as necessary. The amount of the oxidizing agent is usually 1 mol to an excess amount per 1 mol of the compound (26). Examples of the solvent usually used in the reaction include halogenated hydrocarbons such as dichloromethane, dibromomethane, chloroform, bromoform, carbon tetrachloride, 1,2-dichloroethane, chlorobenzene and the like, hydrocarbons such as toluene, benzene, xylene and the like, and a mixture thereof. Examples of the base include metal carbonates such as sodium carbonate, potassium carbonate, sodium hydrogen carbonate, potassium hydrogen carbonate, calcium carbonate, cesium carbonate and the like. The amount of the base used is usually 1 mol or more per 1 mol of the compound (26).

In the case of using air as the oxidizing agent, the reaction is performed in the presence of a solvent and a catalyst as necessary. Examples of the solvent usually used in the reaction include halogenated hydrocarbons such as dichloromethane, dibromomethane, chloroform, carbon tetrachloride, 1,2-dichloroethane, chlorobenzene and the like, hydrocarbons such as toluene, benzene, xylene and the like, and a mixture thereof. Examples of the catalyst include metal halides such as iron(III) chloride, iron(III) bromide and the like. The amount of the catalyst used is usually 0.001 to 1 mol per 1 mol of the compound (26).

The compound (1), the compound (2) and their intermediate compounds described above can be isolated and purified by a conventional method such as liquid separation, filtration, recrystallization, column chromatography, high performance column chromatography (HPLC), medium pressure preparative HPLC, desalting resin column chromatography, re-precipitation, distillation or the like.

Then, each substituent represented by $R^1$, $R^2$, $R^3$, $R^4$, $R^5$, $R^6$ and $R^7$ in the compound (1), the compound (2) and the compound (3) will be explained.

Examples of the "halogen atom" include a fluorine atom, a chlorine atom, a bromine atom and an iodine atom.

Examples of the "C1-C6 alkyl group optionally substituted with at least one halogen atom" include a methyl group, a trifluoromethyl group, a trichloromethyl group, a chloromethyl group, a dichloromethyl group, a fluoromethyl group, a difluoromethyl group, an ethyl group, a pentafluoroethyl group, a 2,2,2-trifluoroethyl group, a 2,2,2-trichloroethyl group, a propyl group, an isopropyl group, a heptafluoroisopropyl group, a butyl group, an isobutyl group, a sec-butyl group, a tert-butyl group, a pentyl group and a hexyl group.

Examples of the "C3-C6 alkoxyalkyl group optionally substituted with at least one halogen atom" include a 2-methoxyethyl group, a 2-ethoxyethyl group and a 2-isopropyloxyethyl group.

Examples of the "C2-C6 alkenyl group optionally substituted with at least one halogen atom" include a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group.

Examples of the "C3-C6 alkynyl group optionally substituted with at least one halogen atom" include a 2-propynyl group, a 3-chloro-2-propynyl group, a 3-bromo-2-propynyl group, a 2-butynyl group and a 3-butynyl group.

Examples of the "C1-C6 alkoxy group optionally substituted with at least one halogen atom" include a methoxy group, an ethoxy group, a 2,2,2-trifluoroethoxy group, a propoxy group, an isopropyloxy group, a butoxy group, an isobutyloxy group, a sec-butoxy group and a tert-butoxy group.

Examples of the "C1-C6 alkylthio group optionally substituted with at least one halogen atom" include a methylthio group, a trifluoromethylthio group, an ethylthio group, a propylthio group, an isopropylthio group, a butylthio group, an isobutylthio group, a sec-butylthio group, a tert-butylthio group, a pentylthio group and a hexylthio group.

Example of the "C1-C6 alkylsulfinyl group optionally substituted with at least one halogen atom" include a methylsulfinyl group, a trifluoromethylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group and a hexylsulfinyl group.

Examples of the "C1-C6 alkylsulfonyl group optionally substituted with at least one halogen atom" include a methylsulfonyl group, a trifluoromethylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group and a hexylsulfonyl group.

Examples of the compound (1) include the following aspects:

a compound represented by the formula (1) wherein $R^2$ is a C1-C6 alkyl group optionally substituted with at least one halogen atom;

a compound represented by the formula (1) wherein $R^2$ is a hydrogen atom;

a compound represented by the formula (1) wherein $R^1$ is a methyl group or an ethyl group and $R^2$ is a hydrogen atom, a methyl group or an ethyl group;

a compound represented by the formula (1) wherein $R^1$ and $R^2$ are methyl groups;

a compound represented by the formula (1) wherein $R^1$ is a methyl group and $R^2$ is a hydrogen atom;

a compound represented by the formula (1) wherein $R^1$ is an ethyl group and $R^2$ is a hydrogen atom;

a compound represented by the formula (1) wherein $R^3$ is a C1-C6 alkyl group optionally substituted with at least one halogen atom;

a compound representedby the formula (1) wherein $R^3$ is a methyl group or an ethyl group;

a compound represented by the formula (1) wherein $R^4$ is a halogen atom or a methyl group;

a compound represented by the formula (1) wherein $R^5$ is a halogen atom or a cyano group;

a compound represented by the formula (1) wherein $R^4$ is a halogen atom or a methyl group and $R^5$ is a halogen atom or a cyano group;

a compound represented by the formula (1) wherein $R^1$ is a methyl group or an ethyl group, $R^2$ is a hydrogen atom, a methyl group or an ethyl group, $R^3$ is a methyl group or an ethyl group, $R^4$ is a halogen atom or a methyl group, and $R^5$ is a halogen atom or a cyano group;

a compound represented by the formula (1) wherein $R^1$, $R^2$ and $R^3$ are methyl groups, $R^4$ is a chlorine atom, a bromine atom or a methyl group, and $R^5$ is a chlorine atom, a bromine atom or a cyano group;

a compound represented by the formula (1) wherein $R^1$ is a methyl group, $R^2$ is a hydrogen atom, $R^3$ is a methyl group, $R^4$ is a chlorine atom, a bromine atom or a methyl group, and $R^5$ is a chlorine atom, a bromine atom or a cyano group; and a compound represented by the formula (1) wherein $R^1$ is an ethyl group, $R^2$ is a hydrogen atom, $R^3$ is a methyl group, $R^4$ is a chlorine atom, a bromine atom or a methyl group, and $R^5$ is a chlorine atom, a bromine atom or a cyano group.

Examples of the compound (2) include the following aspects:

a compound represented by the formula (2) wherein $R^6$ is a halogen atom or a C1-C6 alkyl group optionally substituted with at least one halogen atom;

a compound represented by the formula (2) wherein $R^6$ is a halogen atom or a trifluoromethyl group;

a compound represented by the formula (2) wherein $R^7$ is a halogen atom;

a compound represented by the formula (2) wherein $R^6$ is a halogen atom or a trifluoromethyl group and $R^7$ is a halogen atom; and a compound represented by the formula (2) wherein $R^6$ is a chlorine atom, a bromine atom or a trifluoromethyl group and $R^7$ is a chlorine atom.

Examples of the compound (3) include the following aspects:

a compound represented by the formula (3) wherein $R^2$ is a C1-C6 alkyl group optionally substituted with at least one halogen atom;

a compound represented by the formula (3) wherein $R^2$ is a hydrogen atom;

a compound represented by the formula (3) wherein $R^1$ is a methyl group or an ethyl group and $R^2$ is a hydrogen atom, a methyl group or an ethyl group;

a compound represented by the formula (3) wherein $R^1$ and $R^2$ are methyl groups;

a compound represented by the formula (3) wherein $R^1$ is a methyl group and $R^2$ is a hydrogen atom;

a compound represented by the formula (3) wherein $R^1$ is an ethyl group and $R^2$ is a hydrogen atom;

a compound represented by the formula (3) wherein $R^3$ is a C1-C6 alkyl group optionally substituted with at least one halogen atom;

a compound represented by the formula (3) wherein $R^3$ is a methyl group or an ethyl group;

a compound represented by the formula (3) wherein $R^4$ is a halogen atom or a methyl group;

a compound represented by the formula (3) wherein $R^5$ is a halogen atom or a cyano group;

a compound represented by the formula (3) wherein $R^4$ is a halogen atom or a methyl group and $R^5$ is a halogen atom or a cyano group;

a compound represented by the formula (3) wherein $R^6$ is a halogen atom or a C1-C6 alkyl group optionally substituted with at least one halogen atom;

a compound represented by the formula (3) wherein $R^6$ is a halogen atom or a trifluoromethyl group;

a compound represented by the formula (3) wherein $R^7$ is a halogen atom;

a compound represented by the formula (3) wherein $R^6$ is a halogen atom or a trifluoromethyl group and $R^7$ is a halogen atom;

a compound represented by the formula (3) wherein $R^1$ is a methyl group or an ethyl group, $R^2$ is a hydrogen atom, a methyl group or an ethyl group, $R^3$ is a methyl group or an ethyl group, $R^4$ is a halogen atom or a methyl group, $R^5$ is a halogen atom or a cyano group, $R^6$ is a halogen atom or a trifluoromethyl group, and $R^7$ is a halogen atom;

a compound represented by the formula (3) wherein $R^1$, $R^2$ and $R^3$ are methyl groups, $R^4$ is a chlorine atom, a bromine atom or a methyl group, $R^5$ is a chlorine atom, a bromine atom or a cyano group, $R^6$ is a chlorine atom, a bromine atom or a trifluoromethyl group, and $R^7$ is a chlorine atom;

a compound represented by the formula (3) wherein $R^4$ is a methyl group, $R^2$ is a hydrogen atom, $R^3$ is a methyl group, $R^4$ is a chlorine atom, a bromine atom or a methyl group, $R^5$ is a chlorine atom, a bromine atom or a cyano group, $R^6$ is a chlorine atom, a bromine atom or a trifluoromethyl group, and $R^7$ is a chlorine atom; and a compound represented by the formula (3) wherein $R^4$ is an ethyl group, $R^2$ is a hydrogen atom, $R^3$ is a methyl group, $R^4$ is a chlorine atom, a bromine atom or a methyl group, $R^5$ is a chlorine atom, a bromine atom or a cyano group, $R^6$ is a chlorine atom, a bromine atom or a trifluoromethyl group, and $R^7$ is a chlorine atom.

Examples of the compound (17) include the following aspects:

a compound represented by the formula (17) wherein $R^6$ is a halogen atom or a C1-C6 alkyl group optionally substituted with at least one halogen atom;

a compound represented by the formula (17) wherein $R^6$ is a halogen atom or a trifluoromethyl group;

a compound represented by the formula (17) wherein $R^7$ is a halogen atom;

a compound represented by the formula (17) wherein $R^6$ is a halogen atom or a trifluoromethyl group, and $R^7$ is a halogen atom; and a compound represented by the formula (17) wherein $R^6$ is a chlorine atom, a bromine atom or a trifluoromethyl group, and $R^7$ is a chlorine atom.

The compound (3) produced by the process of the present invention has an excellent controlling activity on harmful arthropods. Examples of harmful arthropods that can be controlled by the compound (3) include arthropods as mentioned below.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny white fly (*Aleurocanthus spiniferus*); scales (Coccidae) such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; whites and sulfer butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tuberworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

*Thrips* (Thripidae) such as yellow citrus thrips (*Frankliniella occidentalis*), *Thrips parmi*, yellow tea thrips (*Scirtothrips dorsalis*), onion thrip (*Thrips tabaci*), flower thrips (*Frankliniella intonsa*), etc.

Diptera:

Housefly (*Musca domestica*), common mosquito (*Culex popiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), *Ceratitis capitata*, legume leafminer (*Liriomyza trifolii*), tomato leafminer (*Liriomyza sativae*), garden pea leafminer (*Chromatomyia horticola*), etc.

Coleoptera:

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), *Anthonomus grandis*, azuki bean weevil (*Callosobruchus chinensis*), *Sphenophorus venatus*, Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), etc.

Orthoptera:

Asiatic locust (*Locusta migratoria*), African mole cricket (*Gryllotalpa africana*), rice grasshopper (*Oxya yezoensis*), rice grasshopper (*Oxya japonica*), etc.

Hymenoptera:

Cabbage sawfly (*Athalia rosae*), leaf-cutting ant (*Acromyrmex* spp.), fire ant (*Solenopsis* spp.), etc.

Blattodea:

German cockroach (*Blattella germanica*), smokybrown cockroach (*Periplaneta fuliginosa*), American cockroach (*Periplaneta americana*), *Periplaneta* brunnea, oriental cockroach (*Blatta orientalis*), etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), pink citrus rust mite (*Phyllocoptruta citri*), tomato rust mite (*Aculops lycopersici*), purple tea mite (*Calacarus carinatus*), pink tea rust mite (*Acaphylla theavagran*), and *Eriophyes chibaensis*; tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, *Ixodes ovatus*, *Ixodes persulcatus*, *Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae); etc.

When the compound (3) is used for controlling harmful arthropods, although the compound (3) may be used as it is, a pesticidal composition comprising the compound (3) as an active ingredient is usually used. The pesticidal composition is obtained by mixing the compound (3) with an inert carrier such as a solid carrier, a liquid carrier or a gaseous carrier and further with, if necessary, a surfactant and other pharmaceutical additives to be formulated into a preparation such as an emulsion, an oil preparation, a powder, a granule, a wettable powder, a flowable preparation, a microcapsule, an aerosol, a fumigant, a poison bait, a resin preparation or the like. The pesticidal composition thus obtained usually contains 0.01 to 95% by weight of the compound (3).

Examples of the solid carrier used for formulation include finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier used for formulation include water, alcohols (methanol, ethanol, isopropyl alcohol, butanol, hexanol, benzyl alcohol, ethylene glycol, propylene glycol, phenoxyethanol etc.), ketones (acetone, methyl ethyl ketone, cyclohexanone etc.), aromatic hydrocarbons (toluene, xylene, ethylbenzene, dodecylbenzene, phenylxylylethane, methylnaphthalene etc.), aliphatic hydrocarbons (hexane, cyclohexane, kerosene, gas oil etc.), esters (ethyl acetate, butyl acetate, isopropyl myristate, ethyl oleate, diisopropyl adipate, diisobutyl adipate, propylene glycol monomethyl ether acetate etc.), nitriles (acetonitrile, isobutyronitrile etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol etc.), acid amides (N,N-dimethylformamide, N,N-dimethylacetamide etc.), halogenated hydrocarbons (dichloromethane, trichloroethane, carbon tetrachloride etc.), sulfoxides (dimethyl sulfoxide etc.), propylene carbonate and vegetable oils (soybean oil, cottonseed oil etc.).

Examples of the gaseous carrier used for formulation include fluorocarbon, butane gas, LPG (liquefied petroleum gas), dimethyl ether and carbon dioxide gas.

Examples of the surfactant include nonionic surfactants such as polyoxyethylene alkyl ether, polyoxyethylene alkyl aryl ether, polyethylene glycol fatty acid ester and the like, and anionic surfactants such as alkyl sulfonate salt, alkylbenzene sulfonate salt, alkyl sulfate salt and the like.

Examples of other pharmaceutical additives include a binder, a dispersant, a coloring agent and a stabilizer, and specific examples thereof include casein, gelatin, saccharides (starch, gum arabic, cellulose derivatives, alginic acid etc.), lignin derivatives, bentonite, synthetic water-soluble polymers (polyvinyl alcohol, polyvinylpyrrolidone, polyacrylic acid etc.), PAP (isopropyl acid phosphate), BHT (2,6-di-tert-butyl-4-methylphenol), and BHA (a mixture of 2-tert-butyl-4-methoxyphenol and 3-tert-butyl-4-methoxyphenol).

For controlling harmful arthropods, the compound (3) can be used as it is or as a pesticidal composition containing the compound (3) as described above. Usually, a pesticidal composition containing the compound (3) as described above is used for controlling harmful arthropods. A method for controlling harmful arthropods comprises applying the compound (3) or a pesticidal composition containing the compound (3) to harmful arthropods or a place where harmful arthropods inhabit by the same method as that of applying a known pesticide.

Examples of the place where harmful arthropods inhabit include paddy fields, cultivated lands, orchards, non-crop lands, houses and the like.

Examples of the application method include spraying treatment, soil treatment, seed treatment, water culture medium treatment and the like.

The spraying treatment is a treatment method which comprises treating the plant surfaces or harmful arthropods themselves with an active ingredient and thereby can produce a controlling effect on harmful arthropods. Specific examples of the spraying treatment include spraying treatment to foliage, spraying treatment to tree trunks and the like.

The soil treatment is a treatment method which comprises treating soil or an irrigation liquid with an active ingredient for the purpose of allowing the active ingredient to permeate and transfer into the interior of the plant body of a crop to be protected from damage such as ingestion by harmful arthropods through the root part or the like of the plant, and thereby can protect the crop from damage by harmful arthropods. Specific examples of the soil treatment include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box), seedling raising tray treatment (spraying on a seedling raising tray, irrigation of a seedling raising tray), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

The seed treatment is a treating method which comprises applying an active ingredient directly to or around a seed, a seed tuber or a bulb of a crop to be protected from damage such as ingestion by harmful arthropods and thereby can produce a controlling effect on harmful arthropods. Specific examples of the seed treatment include spraying treatment, spray coating treatment, immersion treatment, impregnation treatment, coating treatment, film coating treatment, and pellet coating treatment.

The water culture medium treatment is a treating method which comprises treating a water culture medium or the like with an active ingredient for the purpose of allowing the active ingredient to permeate and transfer into the interior of the plant body of a crop to be protected from damage such as ingestion by harmful arthropods through the root part or the like of the plant, and thereby can protect the crop from damage by harmful arthropods. Specific examples of the water culture medium treatment include mixing with a water culture medium, incorporation into a water culture medium, and the like.

When a pesticidal composition comprising the compound (3) is used for controlling harmful arthropods in the field of agriculture, the application amount thereof is usually 1 to 10,000 g of the compound (3) per 10,000 m². When a pesticidal composition comprising the compound (3) is in the form of a preparation such as an emulsion, a wettable powder or a flowable preparation, the composition is usually applied after it is diluted with water so that the active ingredient concentration becomes 0.01 to 10,000 ppm. When a pesticidal composition comprising the compound (3) is in the form of a preparation such as a granule or a powder, the composition is usually applied as it is.

Such a pesticidal composition comprising the compound (3) or a water-dilution thereof may be directly sprayed to harmful arthropods or plants such as crops to be protected from harmful arthropods. Alternatively, soil of a cultivated land may be treated with the composition comprising the compound (3) or a water-dilution thereof in order to control harmful arthropods which inhabit the soil.

A pesticidal composition comprising the compound (3) may be in the form of a resin preparation which is processed into a sheet or a string. Such a resin preparation can be applied by winding a crop with a sheet or a string of the resin preparation, putting a string of the resin preparation around a crop so that the crop is surrounded by the string, or laying a sheet of the resin preparation on the soil surface near the root of a crop.

When a pesticidal composition comprising the compound (3) is used for controlling harmful arthropods living in a house (e.g. fly, mosquito, cockroach), the application amount thereof is usually 0.01 to 1,000 mg of the compound (3) per 1 m² in the case of plain surface treatment, and is usually 0.01 to 500 mg of the compound (3) per 1 m³ in the case of space treatment. When a pesticidal composition comprising the compound (3) is in the form of a preparation such as an emulsion, a wettable powder or a flowable preparation, the composition is usually applied after it is diluted with water so that the active ingredient concentration becomes 0.1 to 1,000 ppm. When a pesticidal composition comprising the compound (3) is in the form of a preparation such as an oil preparation, an aerosol preparation, a fumigant or a poison bait, the composition is usually applied as it is.

The compound (3) can be used as an insecticide for crop lands such as cultivated lands, paddy fields, lawns and orchards, or non-crop lands. The compound produced by the process of the present invention can control pests in crop lands and the like where plants including crops and the like listed below are cultivated without causing drug damage to the crops, in some cases.

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), vine, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

Hereinafter, the present invention will be explained in more detail by reference to Examples, but the present invention is not limited to Examples.

EXAMPLES

Example 1

A mixture of 0.33 g of the compound (1-1):

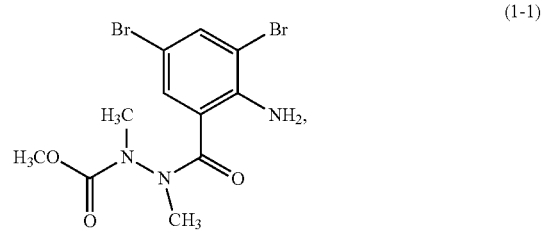 [SMILES: COC(=O)N(C)N(C)C(=O)c1cc(Br)cc(Br)c1N]

(1-1)

0.24 g of the compound (2-1):

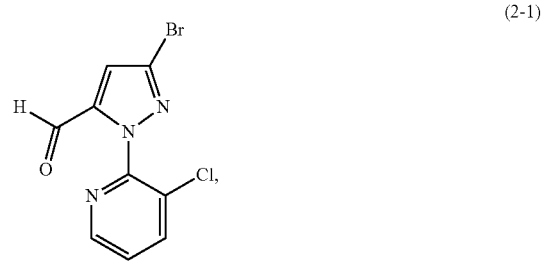 [SMILES: O=Cc1cc(Br)nn1-c1ncccc1Cl]

(2-1)

0.25 g of o-chloranil and 2 ml of 1,4-dioxane was stirred and heated under reflux under a nitrogen atmosphere for 7 hours. The reaction mixture was allowed to cool to room temperature. After an aqueous solution of sodium hydrogen carbonate was added, the reaction mixture was extracted with ethyl acetate. The organic layer was washed with water, dried over anhydrous magnesium sulfate, and concentrated under reduced pressure. The resulting residue was subjected to silica gel column chromatography to obtain 0.35 g of the compound (3-1).

Compound (3-1)

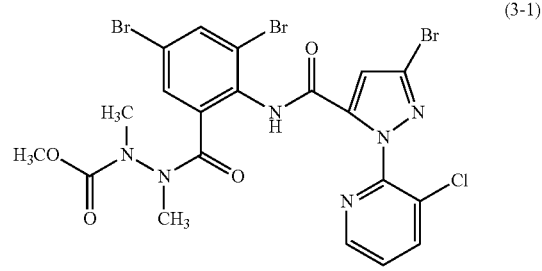

(3-1)

$^1$H-NMR (DMSO-$d_6$, TMS) δ (ppm): 2.71 (1.4H, s), 2.83 (1.6H, s), 2.94 (1.5H, s), 3.06 (1.5H, s), 3.35-3.70 (3.0H, m), 7.41 (0.5H, s), 7.45 (0.6H, s), 7.47 (0.6H, s), 7.60-7.64 (1.3H, m), 8.07 (0.5H, d, J=2 Hz), 8.13 (0.5H, s), 8.18 (1.0H, d, J=8 Hz), 8.50 (1.0H, m), 10.52 (0.5H, s), 10.67 (0.5H, s).

Example 2

A mixture of 0.42 g of the compound (1-1), 0.31 g of the compound (2-1), 0.32 g of p-chloranil, 0.004 g of p-toluenesulfonic acid monohydrate and 3 ml of 1,4-dioxane was stirred and heated under reflux under a nitrogen atmosphere for 4 hours. The reaction mixture was allowed to cool to room temperature. After an aqueous solution of sodium hydrogen carbonate was added, the reaction mixture was extracted with ethyl acetate. The organic layer was washed with water, dried over anhydrous magnesium sulfate, and concentrated under reduced pressure. The resulting residue was subjected to silica gel column chromatography to obtain 0.37 g of the compound (3-1).

Example 3

A mixture of 0.26 g of the compound (1-1), 0.19 g of the compound (2-1), 0.19 g of o-chloranil, 0.017 g of titanium (IV) isopropoxide and 2 ml of 1,4-dioxane was stirred and heated under reflux under a nitrogen atmosphere for 7 hours. The reaction mixture was allowed to cool to room temperature. After an aqueous solution of sodium hydrogen carbonate was added, the reaction mixture was extracted with ethyl acetate. The organic layer was washed with water, dried over anhydrous magnesium sulfate, and concentrated under reduced pressure. The resulting residue was subjected to silica gel column chromatography to obtain 0.20 g of the compound (3-1).

Example 4

A mixture of 0.65 g of the compound (1-2):

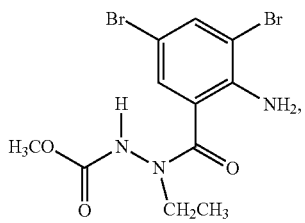

(1-2)

0.47 g of the compound (2-1), 0.48 g of p-chloranil, a catalytic amount of p-toluenesulfonic acid monohydrate and 4 ml of 1,4-dioxane was stirred and heated under reflux under a nitrogen atmosphere for 11 hours. Thereto was added additional 0.20 g of p-chloranil, and the mixture was stirred and heated under reflux for 6 hours. The reaction mixture was allowed to cool to room temperature. After water was added, the reaction mixture was extracted with ethyl acetate. The organic layer was washed with sequentially a 2N sodium hydroxide aqueous solution, water and a saturated sodium chloride aqueous solution, dried over anhydrous magnesium sulfate, and then concentrated under reduced pressure. The resulting residue was subjected to silica gel column chromatography to obtain 0.55 g of the compound (3-2).

Compound (3-2)

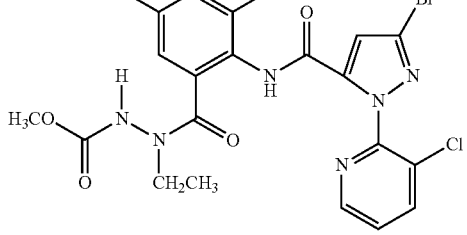

(3-2)

$^1$H-NMR (DMSO-d$_6$, TMS) δ (ppm): 0.86 (1.0H, t, J=7 Hz), 0.99 (2.0H, t, J=7 Hz), 3.10 (1.7H, brs), 3.50 (2.4H, s), 3.64 (0.6H, s), 3.85 (0.3H, brs), 7.36-7.44 (2.0H, m), 7.59-7.65 (1.0H, m), 8.07-8.21 (2.0H, m), 8.49-8.51 (1.0H, m), 9.04 (0.7H, brs), 9.71 (0.3H, brs), 10.30 (0.7H, brs), 10.66 (0.3H, brs).

Example 5

A mixture of 0.096 g of the compound (1-4):

(1-4)

0.072 g of the compound (2-1), 0.075 g of o-chloranil, a catalytic amount of p-toluenesulfonic acid monohydrate, a catalytic amount of copper iodide and 1 ml of 1,4-dioxane was stirred and heated under reflux under a nitrogen atmosphere for 3.5 hours. The reaction mixture was allowed to cool to room temperature. After a 1N aqueous solution of sodium hydroxide was added, the reaction mixture was extracted with ethyl acetate. The organic layer was washed with water, dried over anhydrous magnesium sulfate, and concentrated under reduced pressure. The resulting residue was subjected to silica gel column chromatography to obtain 0.078 g of the compound (3-4).

Compound (3-4)

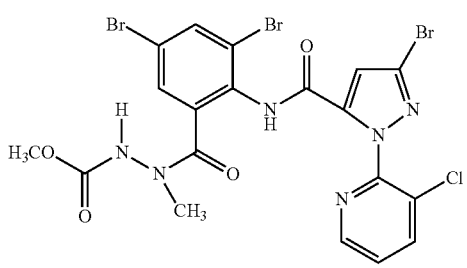

(3-4)

$^1$H-NMR (100° C., DMSO-d$_6$, TMS) δ (ppm): 2.96 (3H, s), 3.04 (3H, brs), 7.30 (1H, s), 7.38 (1H, s), 7.58 (1H, dd, J=8 Hz, 5 Hz), 7.96 (1H, s), 8.11 (1H, d, J=8 Hz), 8.47 (1H, d, J=5 Hz), 8.68 (1H, brs), 10.08 (1H, brs).

Example 6

A mixture of 0.20 g of the compound (1-1), 0.12 g of the compound (2-3):

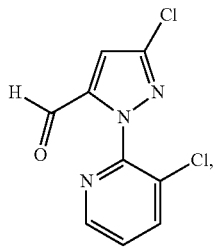

(2-3)

0.15 g of p-chloranil, 0.002 g of p-toluenesulfonic acid monohydrate and 1 ml of 1,4-dioxane was stirred and heated under reflux under a nitrogen atmosphere for 1 hours. The reaction mixture was allowed to cool to room temperature. After a sodium hydrogen carbonate aqueous solution was added, the reaction mixture was extracted with ethyl acetate. The organic layer was washed with water, dried over anhydrous magnesium sulfate, and then concentrated under reduced pressure. The resulting residue was subjected to silica gel column chromatography to obtain 0.21 g of the compound (3-16).

Compound (3-16)

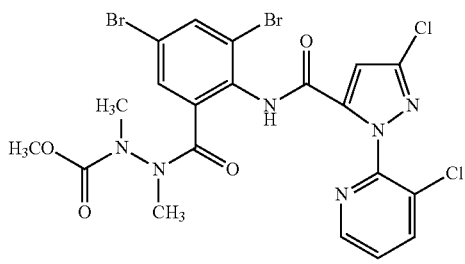

(3-16)

$^1$H-NMR (DMSO-$d_6$, TMS) δ (ppm): 2.71 (1.4H, s), 2.83 (1.6H, s), 2.94 (1.3H, brs), 3.06-3.08 (1.7H, m), 3.44-3.68 (3.0H, m), 7.36-7.47 (2.0H, m), 7.60-7.64 (1.0H, m), 8.08-8.20 (2.0H, m), 8.50-8.51 (1.0H, m), 10.56 (0.4H, brs), 10.71 (0.6H, brs).

Specific examples of the compound (3) which can be produced by the process of the present invention are listed below.

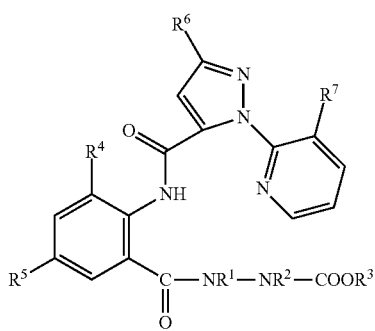

(3)

TABLE 1

| Compound No. | R$^1$ | R$^2$ | R$^3$ | R$^4$ | R$^5$ | R$^6$ | R$^7$ |
|---|---|---|---|---|---|---|---|
| 3-1 | CH$_3$ | CH$_3$ | CH$_3$ | Br | Br | Br | Cl |
| 3-2 | CH$_3$CH$_2$ | H | CH$_3$ | Br | Br | Br | Cl |
| 3-3 | CH$_3$ | H | CH$_3$ | CH$_3$ | Cl | Br | Cl |
| 3-4 | CH$_3$ | H | CH$_3$ | Br | Br | Br | Cl |
| 3-5 | (CH$_3$)$_2$CH | H | CH$_3$ | Br | Br | Br | Cl |
| 3-6 | CH$_3$ | H | CH$_3$ | CH$_3$ | Cl | CF$_3$ | Cl |
| 3-7 | CH$_3$ | CH$_3$ | CH$_3$ | CH$_3$ | Cl | Br | Cl |
| 3-8 | CH$_3$ | H | CH$_3$ | CH$_3$ | CN | Br | Cl |
| 3-9 | CH$_3$ | CH$_3$ | CH$_3$ | CH$_3$ | CN | Br | Cl |
| 3-10 | CH$_3$ | H | CH$_3$ | Cl | Cl | Br | Cl |
| 3-11 | CH$_3$ | H | CH$_3$CH$_2$ | Cl | Cl | Br | Cl |
| 3-12 | CH$_3$ | CH$_3$ | CH$_3$ | Cl | Cl | Br | Cl |
| 3-13 | CH$_3$ | CH$_3$ | CH$_3$ | Br | Cl | Br | Cl |
| 3-14 | CH$_3$ | CH$_3$ | CH$_3$ | CH$_3$ | Cl | Cl | Cl |
| 3-15 | CH$_3$ | CH$_3$ | CH$_3$ | Cl | Cl | Cl | Cl |
| 3-16 | CH$_3$ | CH$_3$ | CH$_3$ | Br | Br | Cl | Cl |
| 3-17 | CH$_3$CH$_2$ | H | CH$_3$ | Cl | Cl | Br | Cl |
| 3-18 | CH$_3$ | CH$_3$ | CH$_3$ | Br | Br | CF$_3$ | Cl |
| 3-19 | CH$_3$(CH$_2$)$_2$ | H | CH$_3$ | Br | Br | Br | Cl |
| 3-20 | CH$_3$ | CH$_3$CH$_2$ | CH$_3$ | Br | Br | Br | Cl |
| 3-21 | CH$_3$CH$_2$ | CH$_3$ | CH$_3$ | Br | Br | Br | Cl |
| 3-22 | CH$_3$CH$_2$ | CH$_3$CH$_2$ | CH$_3$ | Br | Br | Br | Cl |
| 3-23 | CH$_3$CH$_2$ | H | CH$_3$ | CH$_3$ | Cl | Br | Cl |
| 3-24 | CH$_3$CH$_2$ | H | CH$_3$ | CH$_3$ | CN | Br | Cl |
| 3-25 | CH$_3$CH$_2$ | H | CH$_3$ | Br | Br | Cl | Cl |
| 3-26 | CH$_3$CH$_2$ | H | CH$_3$ | Cl | Cl | Cl | Cl |
| 3-27 | CH$_3$CH$_2$ | H | CH$_3$ | CH$_3$ | Cl | Cl | Cl |
| 3-28 | CH$_3$CH$_2$ | H | CH$_3$ | CH$_3$ | CN | Cl | Cl |
| 3-29 | CH$_3$CH$_2$ | H | CH$_3$ | Br | Br | CF$_3$ | Cl |
| 3-30 | CH$_3$CH$_2$ | H | CH$_3$ | Cl | Cl | CF$_3$ | Cl |
| 3-31 | CH$_3$CH$_2$ | H | CH$_3$ | CH$_3$ | Cl | CF$_3$ | Cl |
| 3-32 | CH$_3$CH$_2$ | H | CH$_3$ | CH$_3$ | CN | CF$_3$ | Cl |
| 3-33 | CH$_3$ | H | CH$_3$ | Br | Br | CF$_3$ | Cl |
| 3-34 | CH$_3$ | H | CH$_3$ | Br | Br | Cl | Cl |
| 3-35 | CH$_3$ | H | CH$_3$ | Cl | Cl | Cl | Cl |
| 3-36 | CH$_3$ | H | CH$_3$ | CH$_3$ | Cl | Cl | Cl |
| 3-37 | CH$_3$ | H | CH$_3$ | CH$_3$ | CN | Cl | Cl |
| 3-38 | CH$_3$ | H | CH$_3$ | Cl | Cl | CF$_3$ | Cl |
| 3-39 | CH$_3$ | H | CH$_3$ | CH$_3$ | CN | CF$_3$ | Cl |
| 3-40 | CH$_3$ | CH$_3$ | CH$_3$ | CH$_3$ | CN | Cl | Cl |
| 3-41 | CH$_3$ | CH$_3$ | CH$_3$ | Cl | Cl | CF$_3$ | Cl |
| 3-42 | CH$_3$ | CH$_3$ | CH$_3$ | CH$_3$ | Cl | CF$_3$ | Cl |
| 3-43 | CH$_3$ | CH$_3$ | CH$_3$ | CH$_3$ | CN | CF$_3$ | Cl |

Physical properties of some compounds (3) are shown.

Compound (3-1)

$^1$H-NMR (DMSO-$d_6$, TMS) δ (ppm): 2.71 (1.4H, s), 2.83 (1.6H, s), 2.94 (1.5H, s), 3.06 (1.5H, s), 3.35-3.70 (3.0H, m), 7.41 (0.5H, s), 7.45 (0.6H, s), 7.47 (0.6H, s), 7.60-7.64 (1.3H, m), 8.07 (0.5H, d, J=2 Hz), 8.13 (0.5H, s), 8.18 (1.0H, d, J=8 Hz), 8.50 (1.0H, m), 10.52 (0.5H, s), 10.67 (0.5H, s).

Compound (3-2)

$^1$H-NMR (DMSO-$d_6$, TMS) δ (ppm): 0.86 (1.0H, t, J=7 Hz), 0.99 (2.0H, t, J=7 Hz), 3.10 (1.7H, brs), 3.50 (2.4H, s), 3.64 (0.6H, s), 3.85 (0.3H, brs), 7.36-7.44 (2.0H, m), 7.59-7.65 (1.0H, m), 8.07-8.21 (2.0H, m), 8.49-8.51 (1.0H, m), 9.04 (0.7H, brs), 9.71 (0.3H, brs), 10.30 (0.7H, brs), 10.66 (0.3H, brs).

Compound (3-3)
$^1$H-NMR (CDCl$_3$, TMS) δ (ppm): 2.04 (3H, s), 3.22 (3H, s), 3.57 (2.6H, s), 3.80 (0.4H, s), 7.01 (1H, s), 7.04 (1H, s), 7.28 (1H, s), 7.40 (1H, dd, J=8 Hz, 5 Hz), 7.61 (1H, brs), 7.87 (1H, dd, J=8 Hz, 2 Hz), 8.46 (1H, dd, J=5 Hz, 2 Hz), 9.80 (1H, brs).

Compound (3-4)
$^1$H-NMR (100° C., DMSO-d$_6$, TMS) δ (ppm): 2.96 (3H, s), 3.04 (3H, brs), 7.30 (1H, s), 7.38 (1H, s), 7.58 (1H, dd, J=8 Hz, 5 Hz), 7.96 (1H, s), 8.11 (1H, d, J=8 Hz), 8.47 (1H, d, J=5 Hz), 8.68 (1H, brs), 10.08 (1H, brs).

Compound (3-5)
$^1$H-NMR (CDCl$_3$, TMS) δ (ppm): 0.87-0.95 (3.8H, m), 1.13-1.26 (4.4H, m), 3.55 (2.5H, s), 3.81 (0.5H, s), 4.55-4.67 (1.0H, m), 7.37-7.42 (3.0H, m), 7.49 (1.0H, d, J=2 Hz), 7.57 (1.1H, d, J=2 Hz), 7.86 (1.0H, dd, J=8 Hz, 2 Hz), 8.45 (1.0H, dd, J=5 Hz, 2 Hz), 9.68 (0.3H, brs), 9.93 (0.7H, brs).

Compound (3-6)
$^1$H-NMR (DMSO-d$_6$, TMS) δ (ppm): 2.11 (3H, s), 3.06 (3H, s), 3.33 (3H, s), 7.07 (1H, s), 7.45 (1H, s), 7.68 (1H, s), 7.69 (1H, dd, J=8 Hz, 4 Hz), 8.24 (1H, d, J=8 Hz), 8.55 (1H, d, J=4 Hz), 9.11 (0.6H, brs), 10.20 (1H, brs), 10.54 (0.4H, brs).

Compound (3-7)
$^1$H-NMR (DMSO-d$_6$, TMS) δ (ppm): 2.10-2.24 (3H, m), 2.61-2.87 (3H, m), 2.90-3.18 (3H, m), 3.45-3.74 (3H, m), 7.12-7.30 (1H, m), 7.33-7.44 (1H, m), 7.44-7.58 (1H, m), 7.58-7.66 (1H, m), 8.20 (1H, d, J=8 Hz), 8.47-8.54 (1H, m), 10.10-10.50 (1H, m).

Compound (3-8)
$^1$H-NMR (DMSO-d$_6$, TMS) δ (ppm): 2.21 (3H, s), 3.08 (3H, s), 3.45-3.70 (3H, m), 7.30-7.43 (1H, m), 7.44-7.61 (1H, m), 7.63 (1H, dd, J=8 Hz, 5 Hz), 7.82-7.94 (1H, m), 8.21 (1H, d, J=8 Hz, 1 Hz), 8.51 (1H, dd, J=5 Hz, 1 Hz), 9.21 (1H, brs), 10.24 (1H, brs).

Compound (3-9)
$^1$H-NMR (DMSO-d$_6$, TMS) δ (ppm): 2.14-2.29 (3H, m), 2.64-2.87 (3H, m), 2.87-3.15 (3H, m), 3.42-3.73 (3H, m), 7.30-7.45 (1H, m), 7.54-7.81 (2H, m), 7.83-8.01 (1H, m), 8.15-8.24 (1H, m), 8.50 (1H, brs), 10.20-10.68 (1H, m).

Compound (3-10)
$^1$H-NMR (CDCl$_3$, TMS) δ (ppm): 3.12-3.18 (3H, brm), 3.60-3.84 (3H, brm), 7.21-7.22 (2H, m), 7.34 (1H, brs), 7.41 (1H, dd, J=8 Hz, 5 Hz), 7.51 (1H, brs), 7.88 (1H, dd, J=8 Hz, 1 Hz), 8.48 (1H, dd, J=5 Hz, 1 Hz), 9.85 (1H, brs).

Compound (3-11)
$^1$H-NMR (CDCl$_3$, TMS) δ (ppm): 1.11-1.39 (3H, m), 3.12-3.18 (3H, brm), 4.06-4.25 (2H, brm), 7.08-7.22 (2H, m), 7.34 (1H, brs), 7.41 (1H, dd, J=8 Hz, 5 Hz), 7.43 (1H, brs), 7.88 (1H, dd, J=8 Hz, 1 Hz), 8.49 (1H, dd, J=5 Hz, 1 Hz), 9.87 (1H, brs).

Compound (3-12)
$^1$H-NMR (DMSO-d$_6$, TMS) δ (ppm): 2.73 (1.4H, s), 2.83 (1.6H, s), 2.95 (1.6H, s), 3.07 (1.4H, s), 3.49-3.68 (3.0H, m), 7.32-7.44 (2.0H, m), 7.62 (1.0H, dd, J=8 Hz, 5 Hz), 7.85 (0.5H, d, J=2 Hz), 7.92 (0.5H, s), 8.19 (1.0H, dd, J=8 Hz, 1 Hz), 8.49-8.52 (1.0H, m), 10.53 (0.5H, s), 10.71 (0.5H, s).

Compound (3-13)
$^1$H-NMR (DMSO-d$_6$, TMS) δ (ppm): 2.72 (1.4H, s), 2.83 (1.6H, s), 2.94 (1.6H, s), 3.07 (1.4H, s), 3.49-3.68 (3.0H, m), 7.34-7.45 (2.0H, m), 7.60-7.64 (1.0H, m), 7.98 (0.4H, d, J=2 Hz), 8.04 (0.5H, s), 8.19 (1.0H, d, J=8 Hz), 8.49-8.52 (1.0H, m), 10.54 (0.5H, s), 10.70 (0.5H, s).

Compound (3-14)
$^1$H-NMR (DMSO-d$_6$, TMS) δ (ppm): 2.13 (1.4H, s), 2.18 (1.6H, s), 2.73 (1.4H, s), 2.82 (1.6H, s), 2.93-2.96 (1.2H, m), 3.07-3.07 (1.8H, m), 3.43-3.69 (3.0H, m), 7.18-7.32 (2.0H, m), 7.46-7.53 (1.0H, m), 7.60-7.64 (1.0H, m), 8.19 (1.0H, d, J=8 Hz), 8.49-8.51 (1.0H, m), 10.20 (0.4H, brs), 10.45 (0.6H, brs).

Compound (3-15)
$^1$H-NMR (DMSO-d$_6$, TMS) δ (ppm): 2.73 (1.3H, s), 2.84 (1.7H, s), 2.95 (1.3H, brs), 3.07-3.08 (1.7H, m), 3.46-3.68 (3.0H, m), 7.32-7.39 (2.0H, m), 7.62 (1.0H, dd, J=8 Hz, 5 Hz), 7.85-7.92 (1.0H, m), 8.19 (1.0H, d, J=8 Hz), 8.49-8.51 (1.0H, m), 10.54 (0.4H, brs), 10.74 (0.6H, brs).

Compound (3-16)
$^1$H-NMR (DMSO-d$_6$, TMS) δ (ppm): 2.71 (1.4H, s), 2.83 (1.6H, s), 2.94 (1.3H, brs), 3.06-3.08 (1.7H, m), 3.44-3.68 (3.0H, m), 7.36-7.47 (2.0H, m), 7.60-7.64 (1.0H, m), 8.08-8.20 (2.0H, m), 8.50-8.51 (1.0H, m), 10.56 (0.4H, brs), 10.71 (0.6H, brs).

Compound (3-17)
$^1$H-NMR (CDCl$_3$, TMS) δ (ppm): 1.03-1.07 (3.0H, m), 3.31-3.82 (5.0H, m), 7.23 (2.0H, s), 7.31 (1.0H, s), 7.39 (1.0H, dd, J=8 Hz, 5 Hz), 7.54 (1.0H, s), 7.87 (1.0H, dd, J=8 Hz, 1 Hz), 8.46 (1.0H, dd, J=5 Hz, 1 Hz), 9.65 (0.2H, brs), 9.86 (0.8H, brs).

Compound (3-18)
$^1$H-NMR (DMSO-d$_6$, TMS) δ (ppm): 2.71 (1.4H, s), 2.84 (1.6H, s), 2.95 (1.3H, brs), 3.07 (1.7H, s), 3.45-3.70 (3.0H, brm), 7.48 (1.0H, brs), 7.66-7.71 (1.0H, m), 7.77-7.80 (1.0H, m), 8.12 (1.0H, d, J=21 Hz), 8.24 (1.0H, dd, J=8 Hz, 1 Hz), 8.53-8.55 (1.0H, m), 10.72 (0.4H, brs), 10.85 (0.6H, brs).

Compound (3-19)
$^1$H-NMR (CDCl$_3$, TMS) δ (ppm): 0.88-0.95 (3H, m), 1.48 (2H, tq, J=8 Hz, 8 Hz), 3.22-3.83 (5H, brm), 7.37-7.44 (3H, m), 7.56 (1H, d, J=2 Hz), 7.61 (1H, s), 7.86 (1H, dd, J=8 Hz, 2 Hz), 8.46 (1H, dd, J=5 Hz, 2 Hz), 9.77 (0.3H, s), 9.98 (0.7H, s).

Compound (3-20)
$^1$H-NMR (DMSO-d$_6$, TMS) δ (ppm): 0.79-1.00 (3.0H, m), 2.88 (2.2H, d, J=12 Hz), 3.01-3.08 (1.0H, m), 3.12 (0.8H, s), 3.15-3.22 (1.0H, m), 3.45-3.69 (3.0H, m), 7.41-7.47 (2.0H, m), 7.60-7.64 (1.0H, m), 8.10-8.20 (2.0H, m), 8.49-8.52 (1.0H, m), 10.50 (0.3H, brs), 10.70 (0.7H, brs).

Compound (3-21)
$^1$H-NMR (DMSO-d$_6$, TMS) δ (ppm): 0.86-0.91 (2.0H, m), 1.11-1.14 (1.0H, m), 2.75 (1.0H, s), 2.85-3.23 (4.0H, brm), 3.64-3.73 (3.0H, m), 7.41-7.46 (2.0H, m), 7.60-7.63 (1.0H, m), 8.07-8.19 (2.0H, m), 8.48-8.50 (1.0H, m), 10.48 (0.3H, brs), 10.67 (0.7H, brs).

Compound (3-22)
$^1$H-NMR (DMSO-d$_6$, TMS) δ (ppm): 0.86-1.15 (6.0H, brm), 3.08-3.29 (3.0H, brm), 3.37-3.74 (4.0H, brm), 7.43-7.47 (2.0H, m), 7.61-7.65 (1.0H, m), 8.10-8.20 (2.0H, m), 8.49-8.51 (1.0H, m), 10.47 (0.3H, brs), 10.65-10.76 (0.7H, brm).

Compound (3-23)
$^1$H-NMR (CDCl$_3$, TMS) δ (ppm): 1.06 (3H, t, J=7 Hz), 2.04 (3H, s), 3.56-3.78 (5H, m), 7.02 (1H, s), 7.06 (1H, s), 7.20-7.26 (1H, m), 7.38 (1H, dd, J=8 Hz, 5 Hz), 7.62 (1H, s), 7.86 (1H, dd, J=8 Hz, 2 Hz), 8.44 (1H, dd, J=5 Hz, 2 Hz), 9.82 (1H, brs).

Compound (3-25)
$^1$H-NMR (CDCl$_3$, TMS) δ (ppm): 1.04 (3H, t, J=7 Hz), 3.45-3.90 (5H, m), 7.23 (1H, s), 7.40 (1H, dd, J=8 Hz, 5 Hz), 7.45 (1H, d, J=2 Hz), 7.54 (1H, s), 7.60 (1H, d, J=2 Hz), 7.87 (1H, dd, J=8 Hz, 2 Hz), 8.46 (1H, dd, J=5 Hz, 2 Hz), 9.67 (1H, brs).

Compound (3-26)

¹H-NMR (CDCl₃, TMS) δ (ppm): 1.05 (3H, t, J=7 Hz), 3.43-3.69 (5H, m), 7.19-7.22 (3H, m), 7.40 (1H, dd, J=8 Hz, 5 Hz), 7.53 (1H, s), 7.87 (1H, d, J=8 Hz), 8.46 (1H, d, J=5 Hz), 9.82 (1H, brs).

Compound (3-27)

¹H-NMR (CDCl₃, TMS) δ (ppm): 1.06 (3H, t, J=7 Hz), 2.04 (3H, s), 3.45-3.95 (5H, m), 7.02 (1H, s), 7.06 (1H, s), 7.17 (1H, s), 7.38 (1H, dd, J=8 Hz, 5 Hz), 7.63 (1H, s), 7.86 (1H, dd, J=8 Hz, 2 Hz), 8.44 (1H, dd, J=5 Hz, 2 Hz), 9.83 (1H, brs).

Compound (3-29)

¹H-NMR (CDCl₃, TMS) δ (ppm): 1.04 (3H, t, J=7 Hz), 3.41-3.83 (5H, m), 7.42-7.45 (2H, m), 7.55-7.58 (2H, m), 7.70 (1H, s), 7.89 (1H, dd, J=8 Hz, 2 Hz), 8.48 (1H, dd, J=5 Hz, 2 Hz), 10.20 (1H, brs).

Compound (3-30)

¹H-NMR (CDCl₃, TMS) δ (ppm): 1.05 (3H, t, J=7 Hz), 3.45-3.95 (5H, m), 7.35 (1H, s), 7.39 (1H, dd, J=8 Hz, 5 Hz), 7.43 (1H, d, J=2 Hz), 7.55-7.59 (2H, m), 7.86 (1H, dd, J=8 Hz, 2 Hz), 8.46 (1H, dd, J=5 Hz, 2 Hz), 9.86 (1H, brs).

Compound (3-31)

¹H-NMR (CDCl₃, TMS) δ (ppm): 1.05 (3H, t, J=7 Hz), 1.99 (3H, s), 3.45-3.95 (5H, m), 6.97 (1H, s), 7.04 (1H, s), 7.42 (1H, dd, J=8 Hz, 5 Hz), 7.65 (1H, s), 7.67 (1H, s), 7.88 (1H, d, J=8 Hz), 8.46 (1H, d, J=5 Hz), 10.27 (1H, brs).

Compound (3-33)

¹H-NMR (CDCl₃, TMS) δ (ppm): 3.18 (3H, s), 3.60-3.85 (3H, m), 7.42-7.46 (2H, m), 7.55-7.58 (2H, m), 7.72 (1H, s), 7.90 (1H, dd, J=8 Hz, 2 Hz), 8.49 (1H, dd, J=5 Hz, 2 Hz), 10.14 (1H, brs).

Then, examples of production of the compound (1) and the compound (2) will be described as Reference Production Examples.

Reference Production Example 1

(1) To a mixture of 1.85 g of methyl carbazate and 60 ml of tetrahydrofuran was added 6.0 g of 6,8-dibromo-2H-3,1-benzoxazine-2,4-1H-dione

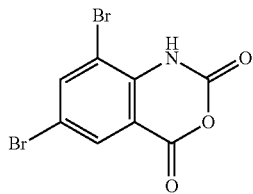

(a compound described in Journal of Organic Chemistry (1947), 12, 743-51) under ice-cooling, and the mixture was stirred for 3 hours under ice-cooling. The reaction mixture was warmed to room temperature, and 0.46 g of methyl carbazate was further added thereto. The mixture was stirred at room temperature for 15 hours, and then concentrated under reduced pressure. To the resulting residue was added water, and the remaining solid was filtered. The solid was washed sequentially with water and ethyl acetate to obtain 4.96 g of N-(2-amino-3,5-dibromobenzoyl)-N'-methoxycarbonylhydrazine.

N-(2-amino-3,5-dibromobenzoyl)-N'-methoxycarbonylhydrazine

¹H-NMR (DMSO-d₆) δ: 3.63 (3H, s), 6.55 (2H, s), 7.71 (1H, s), 7.79 (1H, s), 9.25 (1H, s), 10.32 (1H, s).

(2) To a mixture of 3.67 g of N-(2-amino-3,5-dibromobenzoyl)-N'-methoxycarbonylhydrazine, 3.04 g of potassium carbonate and 50 ml of N-methylpyrrolidone was added dropwise a mixture of 3.12 g of methyl iodide and 2 ml of 1-methyl-2-pyrrolidinone under ice-cooling. The mixture was stirred for 4 hours under ice-cooling, and then stirred at room temperature for 3 hours. After water was added, the reaction mixture was extracted with ethyl acetate. The organic layer was washed with water, dried over anhydrous magnesium sulfate, and concentrated under reduced pressure. The resulting residue was subjected to silica gel column chromatography to obtain 2.83 g of the compound (1-1).

Compound (1-1)

¹H-NMR (CDCl₃, TMS) δ (ppm): 3.11-3.18 (6H, m), 3.76 (3H, brs), 4.86 (1.4H, brs), 5.23 (0.6H, brs), 7.17-7.25 (1H, m), 7.57 (1H, d, J=2 Hz).

Reference Production Example 2

(1) To a mixture of 0.61 g of ethylhydrazine oxalate, 1.0 g of 6,8-dibromo-2H-3,1-benzoxazine-2,4-1H-dione and 10 ml of tetrahydrofuran was added 1.12 g of potassium carbonate under ice-cooling, and the mixture was stirred at room temperature for 1.5 hours. After water was added, the reaction mixture was extracted with ethyl acetate. The organic layer was washed sequentially with water and a saturated solution of sodium chloride, dried over anhydrous magnesium sulfate, and concentrated under reduced pressure. The resulting residue was subjected to silica gel column chromatography to obtain 0.44 g of N-(2-amino-3,5-dibromobenzoyl)-N-ethylhydrazine and 0.13 g of N-(2-amino-3,5-dibromobenzoyl)-N'-ethylhydrazine.

N-(2-amino-2-3,5-dibromobenzoyl)-N-ethylhydrazine

¹H-NMR (CDCl₃, TMS) δ (ppm): 1.25 (3H, t, J=7 Hz), 3.52 (2H, q, J=7 Hz), 4.38 (2H, brs), 4.81 (2H, brs), 7.21 (1H, d, J=2 Hz), 7.59 (1H, d, J=2 Hz).

N-(2-amino-2,3,5-dibromobenzoyl)-N'-ethylhydrazine

¹H-NMR (CDCl₃, TMS) δ (ppm): 1.15 (3H, t, J=7 Hz), 2.95 (2H, q, J=7 Hz), 4.78 (1H, brs), 6.02 (2H, brs), 7.38 (1H, d, J=2 Hz), 7.52 (1H, brs), 7.64 (1H, d, J=2 Hz).

(2) To a mixture of 0.42 g of N-(2-amino-3,5-dibromobenzoyl)-N-ethylhydrazine and 3 ml of pyridine was added 0.15 g of methyl chloroformate under ice-cooling, and the mixture was stirred for 1 hour under ice-cooling. After water was added, the reaction mixture was concentrated under reduced pressure. Water was added to the resulting residue, followed by extraction with ethyl acetate. The organic layer was washed sequentially with water and a saturated solution of sodium chloride, dried over anhydrous magnesium sulfate, and concentrated under reduced pressure. The resulting residue was subjected to silica gel column chromatography to obtain 0.42 g of the compound (1-2).

Compound (1-2)

¹H-NMR (CDCl₃, TMS) δ (ppm): 1.21 (3H, t, J=7 Hz), 3.62 (2H, q, J=7 Hz), 3.78 (3H, s), 4.95 (2H, brs), 6.96 (1H, brs), 7.26 (1H, d, J=2 Hz), 7.59 (1H, d, J=2 Hz).

Reference Production Example 3

(1) To a mixture of 10.0 g of 6,8-dibromo-2H-3,1-benzoxazine-2,4-1H-dione and 90 ml of tetrahydrofuran was added 1.58 g of methylhydrazine under ice-cooling, and the mixture was stirred at room temperature for 4 hours. After water was added, the reaction mixture was extracted with ethyl acetate. The organic layer was washed with a saturated solution of sodium chloride, dried over anhydrous magnesium sulfate, and concentrated under reduced pressure. The resulting residue was subjected to silica gel column chromatography to obtain 4.64 g of N-(2-amino-3,5-dibromobenzoyl)-N-methylhydrazine and 0.75 g of N-(2-amino-3,5-dibromobenzoyl)-N'-methylhydrazine.

N-(2-amino-3,5-dibromobenzoyl)-N-methylhydrazine $^1$H-NMR (CDCl$_3$, TMS) δ (ppm): 3.25 (3H, s), 4.55 (2H, brs), 4.89 (2H, brs), 7.23 (1H, s), 7.59 (1H, s).

N-(2-amino-3,5-dibromobenzoyl)-N'-methylhydrazine $^1$H-NMR (DMSO-d$_6$, TMS) δ (ppm): 2.51 (3H, s), 5.11 (1H, brs), 6.54 (2H, s), 7.63 (1H, d, J=2 Hz), 7.73 (1H, d, J=2 Hz), 10.06 (1H, brs).
(2) To a mixture of 3.40 g of N-(2-amino-3,5-dibromobenzoyl)-N-methylhydrazine and 30 ml of tetrahydrofuran were added 2.2 g of triethylamine and 2.0 g of methyl chloroformate under ice-cooling, and the mixture was stirred at room temperature. After water was added, the reaction mixture was extracted with ethyl acetate. The organic layer was washed with a saturated solution of sodium chloride, dried over anhydrous magnesium sulfate, and concentrated under reduced pressure. The resulting residue was subjected to silica gel column chromatography to obtain 1.10 g of the compound (1-4).
Compound (1-4)
$^1$H-NMR (CDCl$_3$, TMS) δ (ppm): 3.28 (3H, s), 3.76 (3H, s), 4.96 (2H, brs), 7.00 (1H, brs), 7.27 (1H, d, J=2 Hz), 7.59 (1H, d, J=2 Hz).

Reference Production Example 4

(1) A mixture of 10.7 g of 3-bromo-1H-pyrazole, 11.8 g of 2,3-dichloropyridine, 57.3 g of cesium carbonate and 80 ml of N,N-dimethylformamide was stirred at 100° C. for 8 hours. The reaction mixture was allowed to cool to room temperature. After water was added, and the reaction mixture was extracted with methyl tert-butyl ether two times. The organic layers were combined, washed with sequentially with water and a saturated solution of sodium chloride, dried over magnesium sulfate, and concentrated under reduced pressure. The resulting residue was subjected to silica gel column chromatography to obtain 12.9 g of 2-(3-bromo-1H-pyrazol-1-yl)-3-chloropyridine.

2-(3-Bromo-1H-pyrazol-1-yl)-3-chloropyridine $^1$H-NMR (CDCl$_3$, TMS) δ (ppm): 6.51 (1H, d, J=2 Hz), 7.31 (1H, dd, J=8 Hz, 4 Hz), 7.91 (1H, dd, J=8 Hz, 1 Hz), 8.04 (1H, d, J=2 Hz), 8.45 (1H, dd, J=4 Hz, 1 Hz).
(2) To a mixture of 5.0 g of 2-(3-bromo-1H-pyrazol-1-yl)-3-chloropyridine and 30 ml of tetrahydrofuran was added dropwise 11.7 ml of a 2.0M solution of lithium diisopropylamide in heptane/tetrahydrofuran/ethylbenzene. To the reaction mixture was added dropwise a mixture of 3 g of ethyl formate and 10 ml of tetrahydrofuran at −78° C., and the mixture was stirred at room temperature for 2 hours. After water was added, the reaction mixture was extracted with ethyl acetate. The organic layer was washed with water, dried over anhydrous magnesium sulfate, and concentrated under reduced pressure. The resulting residue was subjected to silica gel column chromatography to obtain 3.0 g of the compound (2-1).
Compound (2-1)
$^1$H-NMR (CDCl$_3$, TMS) δ (ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s).

Reference Production Example 5

(1) According to the process of Reference Production Example 4(1) except that 3-trifluoromethyl-1H-pyrazole was used in place of 3-bromo-1H-pyrazole, 3-chloro-2-(3-trifluoromethyl-1H-pyrazol-1-yl)pyridine was obtained.

3-Chloro-2-(3-trifluoromethyl-1H-pyrazol-1-yl)pyridine $^1$H-NMR (CDCl$_3$, TMS) δ (ppm): 6.75 (1H, d, J=2 Hz), 7.37 (1H, dd, J=8 Hz, 4 Hz), 7.95 (1H, dd, J=8 Hz, 1 Hz), 8.14 (1H, d, J=1 Hz), 8.49 (1H, dd, J=4 Hz, 1 Hz).
(2) According to the process of Reference Production Example 4(2) except that 3-chloro-2-(3-trifluoromethyl-1H-pyrazol-1-yl)pyridine is used in place of 2-(3-bromo-1H-pyrazol-1-yl)-3-chloropyridine, the compound (2-2) was obtained.

Compound (2-2)

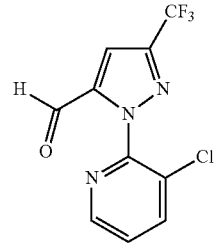

(2-2)

$^1$H-NMR (CDCl$_3$, TMS) δ (ppm): 7.36 (1H, s), 7.51 (1H, dd, J=8 Hz, 5 Hz), 7.99 (1H, dd, J=8 Hz, 2 Hz), 8.54 (1H, dd, J=5 Hz, 2 Hz), 9.86 (1H, s).

Reference Production Example 6

(1) According to the process of Reference Production Example 4(1) except that 3-chloro-1H-pyrazole was used in place of 3-bromo-1H-pyrazole, 2-(3-chloro-1H-pyrazol-1-yl)-3-chloropyridine was obtained.

2-(3-Chloro-1H-pyrazol-1-yl)-3-chloropyridine $^1$H-NMR (CDCl$_3$, TMS) δ (ppm): 6.43 (1H, d, J=3 Hz), 7.30 (1H, dd, J=8 Hz, 5 Hz), 7.91 (1H, dd, J=8 Hz, 2 Hz), 8.09 (1H, d, J=2 Hz), 8.44 (1H, dd, J=5 Hz, 1 Hz).
(2) According to the process of Reference Production Example 4(2) except that 2-(3-chloro-1H-pyrazol-1-yl)-3-chloropyridine is used in place of 2-(3-bromo-1H-pyrazol-1-yl)-3-chloropyridine, the compound (2-3) was obtained.
Compound (2-3)
$^1$H-NMR (CDCl$_3$, TMS) δ (ppm): 7.02 (1H, s), 7.47 (1H, dd, J=8 Hz, 5 Hz), 7.97 (1H, dd, J=8 Hz, 2 Hz), 8.51 (1H, dd, J=5 Hz, 2 Hz), 9.79 (1H, s).

Reference Production Example 7

(1) To a mixture of 10 g of methyl carbazate and 60 ml of toluene was added dropwise a mixture of 5.86 g of acetaldehyde and 20 ml of toluene at 50° C., and the mixture was stirred for 1 hour. The reaction mixture was cooled with ice, and a solid precipitated was filtered. The solid was dried to obtain 12.1 g of N'ethylidenehydrazinecarboxylic acid methyl ester.

N'-ethylidenehydrazinecarboxylic acid methyl ester $^1$H-NMR (CDCl$_3$, TMS) δ (ppm): 1.99 (3H, d, J=5 Hz), 3.82 (3H, s), 7.24 (1H, q, J=5 Hz), 8.31 (1H, brs).
(2) To a mixture of 5.0 g of N'-ethylidenehydrazinecarboxylic acid methyl ester and 50 ml of tetrahydrofuran were added sequentially 1.95 g of sodium borohydride and 4.2 ml of methanol at 50° C., and the mixture was stirred for 3 hours at 50° C. To the reaction mixture was added 50 ml of methanol at 50° C., and then the mixture was stirred and heated under reflux for 3 hours. The reaction mixture was concentrated under reduced pressure, and 20 ml of chloroform was added to the residue. The mixture was stirred at 50° C. for 10 minutes and then filtered with celite. The resulting filtrate was concentrated under reduced pressure and the residue was subjected to silica gel column chromatography to obtain 3.70 g of N'-ethylhydrazinecarboxylic acid methyl ester.

N'-ethylhydrazinecarboxylic acid methyl ester $^1$H-NMR (DMSO-D$_6$, TMS) δ (ppm): 0.93 (3H, t, J=7 Hz), 2.66-2.73 (2H, m), 3.54 (3H, s), 4.38-4.43 (1H, m), 8.45 (1H, s).
(3) To a mixture of 0.50 g of N'-ethylhydrazinecarboxylic acid methyl ester and 4 ml of tetrahydrofuran was added 1.36 g of 6,8-dibromo-2H-3,1-benzoxadine-2,4-1H-dione at room temperature. The mixture was stirred and heated under reflux for 4 hours, and then cooled to room temperature. After water was added, the reaction mixture was extracted with ethyl acetate. The organic layer was washed with a saturated sodium chloride aqueous solution, dried over anhydrous magnesium sulfate, and then concentrated under reduced pressure. The resulting residue was subjected to silica gel column chromatography to obtain 0.89 g of the compound (1-2).

Reference Production Example 8

(1) A mixture of 1.16 g of 4-methoxycrotonic acid (a compound described in Journal of Organic Chemistry, 1981, 46, 940-948) and 10 ml of diethyl ether was cooled with ice, and thereinto hydrogen chloride gas was introduced. After the mixture was saturated with hydrogen chloride gas, it was allowed to stand at room temperature overnight. A sample obtained from the reaction mixture was subjected to NMR analysis to confirm the production of 3-chloro-4-methoxybutyric acid. All amount of the reaction mixture obtained was used as it is for the following step.

3-Chloro-4-methoxybutyric acid $^1$H-NMR (CDCl$_3$, TMS) δ (ppm): 2.76 (1H, dd, J=17.9 Hz), 3.00 (1H, dd, J=17 Hz, 5 Hz), 3.42 (3H, s), 3.56 (1H, dd, J=10 Hz, 7 Hz), 3.65 (1H, dd, J=10 Hz, 5 Hz), 4.36-4.42 (1H, m).
(2) To the reaction mixture obtained in the above step (1), 2.54 g of oxalyl dichloride was added dropwise under ice-cooling. To the reaction mixture was added a drop of N,N-dimethylformamide, and the mixture was stirred at room temperature for 2 hours. The reaction mixture was concentrated under reduced pressure to obtain 1.45 g of 3-chloro-4-methoxybutyryl chloride.

3-Chloro-4-methoxybutyryl chloride $^1$H-NMR (CDCl$_3$, TMS) δ (ppm): 3.26 (1H, dd, J=18 Hz, 9 Hz), 3.41 (3H, s), 3.49-3.54 (2H, m), 3.66 (1H, dd, J=10 Hz, 5 Hz), 4.35-4.41 (1H, m).
(3) To a mixture of 1.29 g of 3-chloro-2-hydrazinopyridine, 1.07 g of pyridine and 10 ml of N,N-dimethylformamide was added dropwise a mixture of 1.45 g of 3-chloro-4-methoxybutyryl chloride and 5 ml of toluene under ice-cooling. The mixture was stirred at room temperature for 2 hours. After water was added, the reaction mixture was extracted with ethyl acetate. The organic layer was washed with water and a saturated sodium chloride aqueous solution, dried over anhydrous sodium sulfate, and then concentrated under reduced pressure to obtain 1.86 g of the compound (22-1).

Compound (22-1)

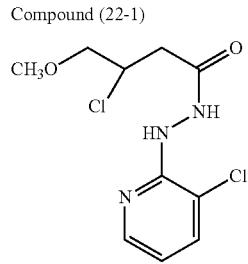

$^1$H-NMR (CDCl$_3$, TMS) δ (ppm): 2.73 (1H, dd, J=15 Hz, 8 Hz), 2.93 (1H, dd, J=15 Hz, 5 Hz), 3.43 (3H, s), 3.63 (1H, dd, J=10 Hz, 6 Hz), 3.71 (1H, dd, J=10 Hz, 5 Hz), 4.47-4.54 (1H, m), 6.78 (1H, dd, J=8 Hz, 5 Hz), 7.35 (1H, brs), 7.56 (1H, dd, J=8 Hz, 1 Hz), 8.07 (1H, dd, J=5.1 Hz), 8.66 (1H, brs).
(4) A mixture of 4.5 g of sodium hydrogen carbonate and 300 ml of N,N-dimethylformamide was heated to 130° C., and thereto was added dropwise a mixture of 7.48 g of the compound (22-1) and 100 ml of N,N-dimethylformamide over 1 hour. The mixture was stirred at 130° C. for 1 hour. After the mixture was allowed to cool, water was added thereto and the mixture was extracted with ethyl acetate. The organic layer was washed sequentially with water and a saturated sodium chloride aqueous solution, dried over sodium sulfate, and then concentrated under reduced pressure. A crystal formed was washed with a small amount of ethyl acetate to obtain 2.02 g of the compound (25-1).

Compound (25-1)

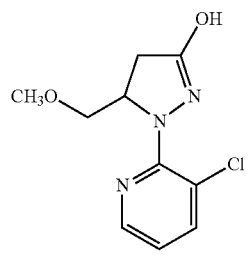

$^1$H-NMR (CDCl$_3$, TMS) δ (ppm): 2.46 (1H, dd, J=17.1 Hz), 2.77 (1H, dd, J=17 Hz, 8 Hz), 3.41 (3H, s), 3.63 (1H, dd, J=10 Hz, 8 Hz), 3.82 (1H, dd, J=10 Hz, 5 Hz), 4.59-4.67 (1H, m), 7.02 (1H, dd, J=8 Hz, 5 Hz), 7.60 (1H, s), 7.68 (1H, dd, J=8 Hz, 2 Hz), 8.20 (1H, dd, J=5 Hz, 2 Hz).

(5) To a mixture of 4.2 g of the compound (25-1), 20 ml of acetonitrile and 1 drop of N,N-dimethylformamide was added 6 g of phosphorus oxybromide at room temperature, and the mixture was heated under reflux for 1 hour. After allowed to cool, the reaction mixture was poured into ice-water and extracted with ethyl acetate. The organic layer was washed with water, dried over anhydrous magnesium sulfate, and then concentrated under reduced pressure. The resulting residue was subjected to silica gel column chromatography to obtain 2.2 g of the compound (26-1).

Compound (26-1)

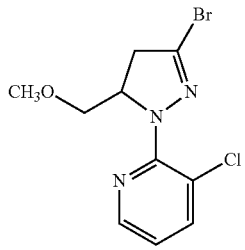

$^1$H-NMR (CDCl$_3$, TMS) δ (ppm): 3.23 (2H, dd, J=10 Hz, 3 Hz), 3.34 (3H, s), 3.48 (1H, dd, J=10 Hz, 6 Hz), 3.66 (1H, dd, J=10 Hz, 4 Hz), 5.01-5.13 (1H, m), 6.91 (1H, dd, J=8 Hz, 5 Hz), 7.66 (1H, dd, J=8 Hz, 2 Hz), 8.17 (1H, dd, J=5 Hz, 2 Hz).

(6) A mixture of 0.10 g of the compound (26-1), 3 ml of acetonitrile, a catalytic amount of copper sulfate and a drop of conc. sulfuric acid was heated to 80° C., and thereto was added dropwise a mixture of 0.14 g of potassium persulfate and 4 ml of water over 2 hours. The mixture was stirred at 80° C. for 10 minutes. After the reaction mixture was allowed to cool, water was added thereto and the mixture was extracted with ethyl acetate. The organic layer was washed with water, dried over anhydrous magnesium sulfate, and then concentrated under reduced pressure. The resulting residue was subjected to silica gel column chromatography to obtain 0.06 g of the compound (17-1).

Compound (17-1)

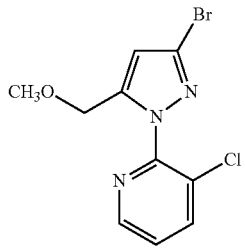

$^1$H-NMR (CDCl$_3$, TMS) δ (ppm): 3.23 (3H, s), 4.50 (2H, s), 6.47 (1H, s), 7.39 (1H, dd, J=8 Hz, 5 Hz), 7.93 (1H, dd, J=8 Hz, 2 Hz), 8.47 (1H, dd, J=5 Hz, 2 Hz).

(7) A mixture of 0.30 g of the compound (17-1), 0.49 g of potassium persulfate, 1 ml of acetonitrile and 1 ml of water was stirred at 90° C. for 12 hours. After the reaction mixture was allowed to cool, water was added thereto and the mixture was extracted with ethyl acetate. The organic layer was washed with water, dried over anhydrous magnesium sulfate, and then concentrated under reduced pressure. The resulting residue was subjected to silica gel column chromatography to obtain 0.16 g of the compound (2-1).

$^1$H-NMR (CDCl$_3$, TMS) δ (ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s).

Reference Production Example 9

(1) To a mixture of 4 g of 4-methoxycrotonic acid and a drop of N,N-dimethylformamide was added dropwise 16.5 g of oxalyl chloride under ice-cooling. The mixture was stirred at room temperature for 2 hours. The reaction mixture was concentrated under reduced pressure to obtain a crude product. All amount of the crude product obtained was used as it is for the following step.

4-Methoxycrotonoyl chloride

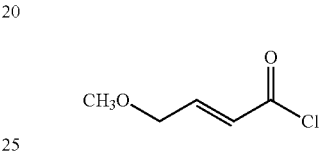

$^1$H-NMR (CDCl$_3$, TMS) δ (ppm): 3.43 (3H, s), 4.18 (2H, dd, J=4 Hz, 2 Hz), 6.34 (1H, dt, J=15 Hz, 2 Hz), 7.19 (1H, dt, J=15 Hz, 4 Hz).

(2) To a mixture of crude product obtained in the above step (1), 50 ml of N,N-dimethyldormamide and 10 g of pyridine at room temperature was added 4.5 g of 3-chloro-2-hydrazinopyridine. The mixture was stirred for 1 hour and then allowed to stand at room temperature overnight. Water was added to the reaction mixture, and the mixture was extracted with ethyl acetate. The organic layer was washed with a saturated ammonium chloride aqueous solution, dried over anhydrous magnesium sulfate, and then concentrated under reduced pressure. A crude crystal formed was washed with a small amount of ethyl acetate to obtain 2.3 g of the compound (24-1).

Compound (24-1)

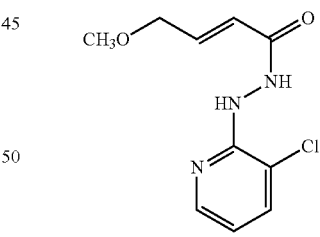

$^1$H-NMR (CDCl$_3$, TMS) δ (ppm): 3.41 (3H, s), 4.10-4.15 (2H, m), 6.21 (1H, dt, J=15 Hz, 2 Hz), 6.76 (1H, dd, J=8 Hz, 5 Hz), 6.98 (1H, dt, J=15 Hz, 4 Hz), 7.48-7.60 (2H, m), 8.07 (1H, dd, J=5 Hz, 1 Hz), 8.45 (1H, brs).

(3) A mixture of 8.0 g of the compound (24-1) and 24.0 g of acetonitrile was cooled with a water bath, and hydrogen chloride gas was introduced thereinto under stirring. After the mixture was stirred while hydrogen chloride gas was introduced for about 3 hours, the reaction mixture was concentrated under reduced pressure. To the resulting residue was added a saturated sodium bicarbonate aqueous solution, and the mixture was extracted with ethyl acetate. The organic layer was washed with a saturated sodium chloride aqueous solution, dried over sodium sulfate, and then concentrated under reduced pressure to obtain 8.97 g of the compound (22-1).

Reference Production Example 10

(1) To a mixture of 0.48 g of the compound (25-1) and 10 ml of acetonitrile were added sequentially 0.25 g of methanesulfonyl chloride and 0.30 g of triethylamine under ice-cooling. The mixture was stirred at 0° C. for 1 hour. Water was added to the reaction mixture, and the mixture was extracted with ethyl acetate. The organic layer was washed with water, dried over anhydrous magnesium sulfate, and then concentrated under reduced pressure. The resulting residue was subjected to silica gel column chromatography to obtain 0.32 g of the compound (27-1).

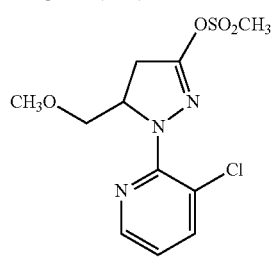

Compound (27-1)

$^1$H-NMR (CDCl$_3$, TMS) δ (ppm): 3.14 (2H, d, J=10 Hz), 3.36 (3H, s), 3.47 (3H, s), 3.55 (1H, dd, J=10 Hz, 6 Hz), 3.66-3.74 (1H, m), 5.10-5.21 (1H, m), 6.87 (1H, dd, J=8 Hz, 5 Hz), 7.64 (1H, dt, J=8 Hz, 1 Hz), 8.14 (1H, dt, J=5 Hz, 1 Hz).
(2) A mixture of 0.53 g of the compound (27-1) and 1.2 g of a 33 wt % solution of hydrogen bromide in acetic acid was stirred at room temperature for 3 hours. The reaction mixture was poured into ice-water, and the mixture was extracted with ethyl acetate. The organic layer was washed with a saturated sodium hydrogen carbonate aqueous solution, dried over anhydrous magnesium sulfate, and then concentrated under reduced pressure. The resulting residue was subjected to silica gel column chromatography to obtain 0.30 g of the compound (26-1).

Then, specific examples of the compounds (1) are listed.

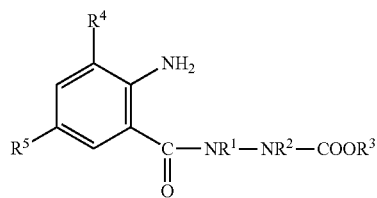

(1)

TABLE 2

| Compound No. | R$^1$ | R$^2$ | R$^3$ | R$^4$ | R$^5$ |
|---|---|---|---|---|---|
| 1-1 | CH$_3$ | CH$_3$ | CH$_3$ | Br | Br |
| 1-2 | CH$_3$CH$_2$ | H | CH$_3$ | Br | Br |
| 1-3 | CH$_3$ | H | CH$_3$ | CH$_3$ | Cl |
| 1-4 | CH$_3$ | H | CH$_3$ | Br | Br |
| 1-5 | (CH$_3$)$_2$CH | H | CH$_3$ | Br | Br |

TABLE 2-continued

| Compound No. | R$^1$ | R$^2$ | R$^3$ | R$^4$ | R$^5$ |
|---|---|---|---|---|---|
| 1-6 | CH$_3$ | CH$_3$ | CH$_3$ | CH$_3$ | Cl |
| 1-7 | CH$_3$ | H | CH$_3$ | CH$_3$ | CN |
| 1-8 | CH$_3$ | CH$_3$ | CH$_3$ | CH$_3$ | CN |
| 1-9 | CH$_3$ | H | CH$_3$ | Cl | Cl |
| 1-10 | CH$_3$ | H | CH$_3$CH$_2$ | Cl | Cl |
| 1-11 | CH$_3$ | CH$_3$ | CH$_3$ | Cl | Cl |
| 1-12 | CH$_3$ | CH$_3$ | CH$_3$ | Br | Cl |
| 1-13 | CH$_3$CH$_2$ | H | CH$_3$ | Cl | Cl |
| 1-14 | CH$_3$(CH$_2$)$_2$ | H | CH$_3$ | Br | Br |
| 1-15 | CH$_3$ | CH$_3$CH$_2$ | CH$_3$ | Br | Br |
| 1-16 | CH$_3$CH$_2$ | CH$_3$ | CH$_3$ | Br | Br |
| 1-17 | CH$_3$CH$_2$ | CH$_3$CH$_2$ | CH$_3$ | Br | Br |
| 1-18 | CH$_3$CH$_2$ | H | CH$_3$ | CH$_3$ | Cl |
| 1-19 | CH$_3$CH$_2$ | H | CH$_3$ | CH$_3$ | CN |

Physical properties of some compounds (1) are shown.
Compound (1-1)
$^1$H-NMR (CDCl$_3$, TMS) δ (ppm): 3.11-3.18 (6H, m), 3.76 (3H, brs), 4.86 (1.4H, brs), 5.23 (0.6H, brs), 7.17-7.25 (1H, m), 7.57 (1H, d, J=2 Hz).
Compound (1-2)
$^1$H-NMR (CDCl$_3$, TMS) δ (ppm): 1.21 (3H, t, J=7 Hz), 3.62 (2H, q, J=7 Hz), 3.78 (3H, s), 4.95 (2H, brs), 6.96 (1H, brs), 7.26 (1H, d, J=2 Hz), 7.59 (1H, d, J=2 Hz).
Compound (1-4)
$^1$H-NMR (CDCl$_3$, TMS) δ (ppm): 3.28 (3H, s), 3.76 (3H, s), 4.96 (2H, brs), 7.00 (1H, brs), 7.27 (1H, d, J=2 Hz), 7.59 (1H, d, J=2 Hz).
Compound (1-15)
$^1$H-NMR (DMSO-d$_6$, 100° C., TMS) δ (ppm): 1.09 (3H, t, J=7 Hz), 3.12 (3H, s), 3.40-3.52 (2H, m), 3.70 (3H, s), 5.23 (2H, brs), 7.20 (1H, d, J=2 Hz), 7.62 (1H, d, J=2 Hz).
Compound (1-16)
$^1$H-NMR (DMSO-d$_6$, 100° C., TMS) δ (ppm): 1.15 (3H, t, J=7 Hz), 3.07 (3H, s), 3.45-3.60 (2H, m), 3.67 (3H, s), 5.19 (2H, brs), 7.20 (1H, d, J=2 Hz), 7.61 (1H, d, J=2 Hz).
Compound (1-17)
$^1$H-NMR (DMSO-d$_6$, 100° C., TMS) δ (ppm): 1.09-1.17 (6H, m), 3.40-3.55 (4H, m), 3.69 (3H, s), 5.19 (2H, brs), 7.22 (1H, d, J=2 Hz), 7.62 (1H, d, J=2 Hz).

Then, specific examples of the compound (2) are listed below.

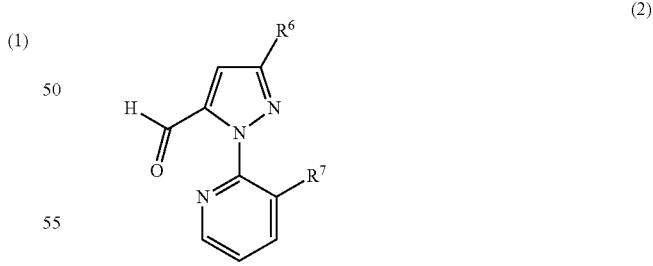

(2)

TABLE 3

| Compound No. | R$^6$ | R$^7$ |
|---|---|---|
| 2-1 | Br | Cl |
| 2-2 | CF$_3$ | Cl |
| 2-3 | Cl | Cl |

Physical properties of some compounds (2) are shown.

Compound (2-1)

$^1$H-NMR (CDCl$_3$, TMS) δ (ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s).

Compound (2-2)

$^1$H-NMR (CDCl$_3$, TMS) δ (ppm): 7.36 (1H, s), 7.51 (1H, dd, J=8 Hz, 5 Hz), 7.99 (1H, dd, J=8 Hz, 2 Hz), 8.54 (1H, dd, J=5 Hz, 2 Hz), 9.86 (1H, s).

Compound (2-3)

$^1$H-NMR (CDCl$_3$, TMS) δ (ppm): 7.02 (1H, s), 7.47 (1H, dd, J=8 Hz, 5 Hz), 7.97 (1H, dd, J=8 Hz, 2 Hz), 8.51 (1H, dd, J=5 Hz, 2 Hz), 9.79 (1H, s).

Then, specific examples of the compound (17) are listed below.

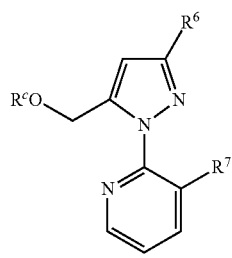

(17)

TABLE 4

| Compound No. | R$^c$ | R$^6$ | R$^7$ |
|---|---|---|---|
| 17-1 | CH$_3$ | Br | Cl |
| 17-2 | CH$_3$ | Cl | Cl |

Physical properties of some compounds (17) are shown.

Compound (17-1)

$^1$H-NMR (CDCl$_3$, TMS) δ (ppm): 3.23 (3H, s), 4.50 (2H, s), 6.47 (1H, s), 7.39 (1H, dd, J=8 Hz, 5 Hz), 7.93 (1H, dd, J=8 Hz, 2 Hz), 8.47 (1H, dd, J=5 Hz, 2 Hz).

Then, examples of formulation of the compound (3) as a pesticidal composition will be described as Reference Formulation Example.

Reference Formulation Example 1

A mixture of 10 parts of any one of the compounds (3-1) to (3-23), (3-25) to (3-27), (3-29) to (3-31) and (3-33), 35 parts of white carbon containing 50 parts of polyoxyethylene alkyl ether sulfate ammonium salt, and 55 parts of water is finely ground by a wet grinding method to obtain a 10% flowable agent.

The following Reference Test Examples demonstrate that the compound (3) is useful as an active ingredient of a pesticidal composition.

Reference test Example 1

Preparations of the compounds (3-1) to (3-23), (3-25) to (3-27), (3-29) to (3-31) and (3-33) obtained in Reference Formulation Example 1 were diluted with water so that the active ingredient concentration became 500 ppm to prepare test spray solutions.

At the same time, a cabbage was planted in a polyethylene cup and grown until the third true leaf or the fourth true leaf was developed. The test spray solution as described above was sprayed in an amount of 20 ml/cup on the cabbage.

After the drug solution sprayed on the cabbage was dried, the cabbage was parasitized with 10 third-instar larvae of diamondback moths (Plutella xylostella) were put on the cabbage. After 5 days, the number of diamondback moths was counted, and a controlling value was calculated by the following equation:

Controlling value (%)={1−(Cb×Tai)/(Cai×Tb)}×100 wherein,

Cb: the number of worms in a non-treated section before treatment

Cai: the number of worms in a non-treated section on observation

Tb: the number of worms in a treated-section before treatment

Tai: the number of worms in a treated-section on observation.

As a result, the test spray solutions of the compounds (3-1) to (3-23), (3-25) to (3-27), (3-29) to (3-31) and (3-33) each exhibited a controlling value of 80% or more.

Reference Test Example 2

Preparations of the compounds (3-1) to (3-23), (3-25) to (3-27), (3-29) to (3-31) and (3-33) obtained in Reference Formulation Example 1 was diluted with water so that the active ingredient concentration became 500 ppm to prepare test spray solutions.

At the same time, a cucumber was planted in a polyethylene cup, and was grown until the first true leaf was developed. About 30 cotton aphids (Aphis gossypii) were put on the cucumber. One day after, the test spray solution as described above was sprayed in an amount of 20 ml/cup on the cucumber. Six days after spraying, the number of cotton aphids was counted, and a controlling value was calculated by the following equation:

Controlling value (%)={1−(Cb×Tai)/(Cai×Tb)}×100 wherein,

Cb: the number of insects in a non-treated section before treatment

Cai: the number of insects in a non-treated section on observation

Tb: the number of insects in a treated-section before treatment

Tai: the number of insects in a treated-section on observation.

As a result, the test spray solutions of the compounds (3-1) to (3-23), (3-25) to (3-27), (3-29) to (3-31) and (3-33) each exhibited a controlling value of 90% or more.

INDUSTRIAL APPLICABILITY

According to the present invention, the compound (3) having an excellent controlling activity on harmful arthropods can be produced.

The invention claimed is:
1. An aniline compound represented by the formula (1):

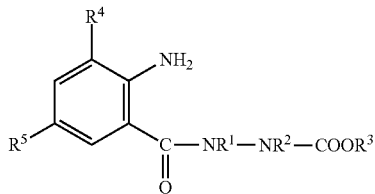

wherein $R^4$ represents a C1-C6 alkyl group optionally substituted with at least one halogen atom, $R^2$ represents a hydrogen atom, or a C1-C6 alkyl group optionally substituted with at least one halogen atom, $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom.

2. The aniline compound according to claim 1, wherein $R^4$ represents a methyl group or an ethyl group, and $R^2$ represents a hydrogen atom, a methyl group or an ethyl group.

3. The aniline compound according to claim 1, wherein $R^1$ and $R^2$ each represent a methyl group.

4. The aniline compound according to claim 1, wherein $R^1$ represents a methyl group and $R^2$ represents a hydrogen atom.

5. The aniline compound according to claim 1, wherein $R^1$ represents an ethyl group and $R^2$ represents a hydrogen atom.

* * * * *